US006242252B1

(12) United States Patent
Reid et al.

(10) Patent No.: US 6,242,252 B1
(45) Date of Patent: **\*Jun. 5, 2001**

(54) HEPATIC PROGENITORS AND METHOD OF ISOLATING SAME

(75) Inventors: Lola M. Reid, Chapel Hill, NC (US); Samuel H. Sigal, Riverdale, NY (US); Shlomo Brill, Ramat-Gan (IL); Patricia A. Holst, Ossining, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/154,222

(22) Filed: Sep. 16, 1998

Related U.S. Application Data

(63) Continuation of application No. 08/757,336, filed on Nov. 27, 1996, now Pat. No. 6,069,005, which is a continuation of application No. 08/548,075, filed on Oct. 25, 1995, now abandoned, which is a continuation of application No. 08/155,939, filed on Nov. 19, 1993, now abandoned, which is a continuation-in-part of application No. 07/741,128, filed on Aug. 7, 1991, now abandoned.

(51) Int. Cl.$^7$ ............................... C12N 5/00; C12N 5/08
(52) U.S. Cl. ........................ 435/325; 435/378; 435/379; 435/380; 435/381
(58) Field of Search ...................................... 435/325, 378, 435/379, 380, 381

(56) References Cited

U.S. PATENT DOCUMENTS

| | | |
|---|---|---|
| 5,030,105 | 7/1991 | Kuri-Harcuch et al. . |
| 5,032,508 | 7/1991 | Naughton et al. . |
| 5,061,620 | 10/1991 | Tsukamoto et al. . |
| 5,087,570 | 2/1992 | Weissman et al. . |
| 5,160,490 | 11/1992 | Naughton et al. . |
| 5,510,254 | 4/1996 | Naughton et al. . |
| 5,559,022 | 9/1996 | Naughton et al. . |
| 5,576,207 | 11/1996 | Reid et al. . |
| 5,624,840 | 4/1997 | Naughton et al. . |
| 5,785,964 | 7/1998 | Naughton et al. . |
| 5,858,721 | 1/1999 | Naughton et al. . |

FOREIGN PATENT DOCUMENTS

94/08598    4/1994  (WO) .

OTHER PUBLICATIONS

Agelli et al., "Survival in Culture of Putative Liver Stem Cells is Independent from Known Epithelial Cell Growth Factors", "*Clinical Research*", , vol. 39 (No. 2), pp. 167A (1991).

Aterman, , "The Stem Cells of Liver–a Selective Review", "*J Cancer Research Clinical Oncol.*", vol. 118, pp. 87–115 (1992).

Barclay, "The Localization of Populations of Lymphocytes Defined by Monoclonal Antibodies in Rat Lymphoid Tissues", "*Immunology*", vol. 42, pp. 593–600, (1981).

Block et al., "Population Expansion, Clonal Growth, and Specific Differentiation Patterns in Primary Cultures of Hepatocytes Induced by HGF/SF, EGF and TGF in a Chemically Defined (HGM) Medium", "*Journal of Cell Biology*", vol. 132 (No. 6), pp. 1331149 (1996).

Brill et al., "Maturation–Dependent Changes in the Regulation of Liver–Specific Gene Expression in Embryonalversus Adult Primary Liver Cultures", "*Differentiation*", vol. 59, pp. 95–102 (1995).

Brill et al., "Extracellular Matrix Regulation of Growth and Gene Expression in Liver Cell Lineages and Hepatomas", "*The Liver: biology and Pathobiology*", pp. 869–891, (1994).

Chomczynski et al., "Single–Step Method of RNA Isolation by Acid Guanidinium Thiocyanate–Phenol–Chloroform Extraction", "*Anal Biochem.*", vol. 162, pp. 156–159 (1987).

Conrad et al., "Combined Cystic Teratoma and Hepatoblastoma of the Liver", "*Cancer*", vol. 72 (No. 10), pp. 2910–2913 (1993).

Cram, "Abstracts for the XIII International Meeting of the Society for Analytical Cytology", "*Journal of Society for Analytical Cytology Cytometry*", Supp. 2, pp. 12 (1988).

Damjanovich et al., "Cyclosporing Depolarizes Human Lymphocytes: Earliest Observed Effect on Cell Metabolism", "*European Journal of Immunology*", vol. 17, pp. 763–768 (1987).

Enat et al., "Hepatocyte Proliferation in Vitro: Its Dependence on the use of Serum–Free Hormonally Defined Medium: and Substrata of Extracellular Matrix", "*Proc. Natl. Acad. of Sci. U.S.A.*", vol. 81, pp. 1411–1415 (1984).

Enjoji et al., "Establishment of a Facultative Human Hepatic Stem Cell Line with a Dual Differentiating Potentiality", "*Gastroenterology 110*", vol. 110 (4 suppl.), A1187 (1996).

Fujio et al., Involvement of Stem Cell Factor and its Receptor, C–Kit, in Liver Regeneration via the Hepatic Stem Cell Compartment "*Hepatology 18*", vol. 18 (No. 4), pp. 161A, (1993).

Fulwyler, "Hydrodynamic Orientation of Cells", "*J Histochemically & Cytochemistry*", vol. 25 (No. 7), pp. 781–783 (1977).

Fulwyler et al., "Production of Uniform Microspheres", "*Review of Scientific Instruments*", vol. 44 (No. 2), pp.204–206 (1973).

(List continued on next page.)

Primary Examiner—Christina Y. Chan
Assistant Examiner—Marianne DiBrino

(57) ABSTRACT

This invention relates to methods of isolating hepatic progenitors utilizing panning techniques and fluorescence activated cell sorting. This invention further relates to isolated hepatic progenitors and to a method of treating liver dysfunction as well as to methods of forming artificial livers.

32 Claims, 11 Drawing Sheets

OTHER PUBLICATIONS

Gebhardt, "Metabolic Zonation of the Liver: Regulation and Implications for Liver Function", *"Pharmac. Ther."*, vol. 23, pp. 275–354 (1990).

Germain et al., "Biliary Epithelial and Hepatocytic Cell Lineage Relationships in Embryonic Rat Liver as Determined by the Differential Expression of Cytokeratins, α–Fetoprotein. Albumin. and Cell–Surface–exposed Components", *"Cancer Research"*, vol. 48, pp. 4909–4918 (1988).

Grisham, "Migration of Hepatocyes Along Hepatic Plates and Stem Cell–Fed Hepatocyte Lineages", *"American J. of Pathology"*, vol. 144 (No. 5), pp. 849–854 (1994).

Grisham et al., Isolation, Culture, and Transplantation of Rat Hepatocytic Precursor (Stem–Like) Cells, *"Culture of Hepatocytic Stem–Like Cells"*, vol. 204 (No. 3), pp. 270–279, (1993).

Hirata et al., "Effects of Basement Membrane Matrix on the Culture of Fetal Mouse Hepatocytes", *"Biol. Abstr."*, Reference No. 57932, vol. 77 (No. 8), pp. 6372, 1984.

Hixon et al., "An Antigenic Portrait of the Liver during Carcinogenesis", *"Pathobiology: Liver Carcinogenesis"*, pp. 65–77 (1990).

Hoang et al., "Separation of Hemopoietic Cells From Adult Mouse Marrow by Use of Monoclonal Antibodies", *"Monoclonals Against Hemopoietic Cells"*, vol. 61, pp. 580–588 (1983).

Johe et al., "Single Factors Direct the Differentiation of Stem Cells from the Fetal and Adult Central Nervous System", *"Genes & Development"*, vol. 10, pp. 3129–3140 (1996).

Li et al., "Culturing of Primary Hepatocytes as Entrapped Aggregates in a Packed Bed Bioreactor: A Potential Bioartificial Liver", *"In Vitro Cell. Dev. Bio."*, vol. 29A, pp. 249–254 (1993).

Reid, "Defining Hormone and Matrix Requirements for Differentiated Epithelia", *"Methods in Molecular Biology"*, The Humana Press, Inc., vol. 5, pp. 237–276 (1990).

Reid, "Stem Cell/Lineage Biology and Lineage–Dependent Extracellular Matrix Chemistry: Keys to Tissue Engineering of Quiescent Tissues such as Liver", *"Textbook of Tissue Engineering"*, pp. 477–509 (1996).

Robinson et al., "MRC OX–43: A Monoclonal Antibody which reacts with all Vascular Endothelium in the rat except that of Brain Capillaries", *"Immunology"*, vol. 57, pp. 231–237 (1986).

Rutenberg et al., "Histochemical and Ultrastructural Demonstration of Glutamyl Transpeptidase Activity", *"Jounal of Histochemistry and Cytochemistry."*, vol. 17, pp. 517–526 (1969).

Sanders et al., Determination of Guanine–plus–cytosine Content of Bacterial DNA by dual–laser Flow Cytometry, *"Journal of General Microbiology"*, vol. 136 (Part 2), pp. 219–376 (1990).

Sanders et al., "Detection and Analysis by Dual–Laser Flow Cytometry of Bacteriophage T4 DNA Inside *Escherichia Coli"*, *"Journal of the Inter. Society for Analytical Cytology Cytometry"*, vol. 12, pp. 167–171 (1991).

Scillian et al., "Early Detection of Antibodies Against rDNA–Produced HIVProteins with a Flow of Cytometric Assay", *"Journal of American Society of Hematology"*, vol. 73 (No. 7), pp. 2041–2048 (1989).

Sigal et al., "Demonstration of Differentiation in Hepatocyte Progenitor Cells Using Dipeptidyl Peptidae IV Deficient Mutant Rats", *"Cellular and Molecular Biology Research"*, vol. 41 (No. 1), pp. 39–47 (1995).

Sigal et al., "Characterization and Enrichment of Fetal Rat Hepatoblasts by Immunoadsorption ("Panning") and Fluorescene–activated Cell Sorting", *"Hepatology"*, vol. 19 (No. 4), pp. 999–1006 (1994).

Sigal et al., "Evidence for a Terminal Differentiation process in the Rat Liver", *"Differentiation"*, vol. 59, pp. 35–42 (1995).

Sigal et al., "The Liver as a Stem Cell and Lineage System", *"American J. of Physiol (Invited Review)"*, pp. G139–G148 (1992).

Szöllösi et al., Physical Association Between MHC Class I and Class II Molecules Detected on the Cell Surface by Flow Cytometric Energy Transfer", *Journal of Immunology"*, vol. 143 (No. 1), pp. 208–213 (1989).

Steinkamp et. al., "A New Multiparameter Separator for Microscopic Particles and Biological Cells", *"Review of Scientific Instruments"*, , vol. 44 (No. 9), pp. 1301–1310 (1973).

Taniguchi et al., "Conditions for theSuccessful Engraftment of Hepatocyte Progenitors Injected into the Spleen", *"Transplantation Proceedings"*, vol 28 (No. 3), pp. 1855–1856, (1996).

Tasi et al., Isolation of a Human Stromal Cell Strain Secreting Hemopoietic Growth Factors, *"Journal of Cellular Physiology"*, vol. 127, pp. 137–145 (1986).

Tsai et al., "Isolation of a Human Stromal Cell Strain Secreting Hemopoietic Growth Factors", *"Biology Abstr."*, Ref. No. 22434, vol. 82 (No. 3).

Gupta et al., "Permanent Engraftment and Function of Hepatocytes Delivered to the Liver; Implications for Gene Therapy and Liver Repopulation", *"Hepetology"*, vol. 14 (No. 1), pp. 144–149 (1991).

Koch, et al., "Retroviral vector infection and transplantation in rats of primary fetal rat Hepatocytes", *"Journal of Cell Sciences"*, vol. 99, pp. 121–130 (1991).

Armentano, et al., "Expression of human factor IX in rabbit hepatocytes by retrovirus–medicated gene transfer: Potential for gene therapy of hemophilia B", *"Proc. Natl. Acad. Sci"*, vol. 87, pp. 6141–6145, (1990).

Wilson et al., "Temporary amelioration of hyperlipidemia in low density lipoprotein receptor–deficient rabbits transplanted with genetically modified hepatocytes", *"Proc. Natl. Acad. Sci"*, vol. 87, pp.8437–8440 (1990).

Ledley et al., "Retroviral gene transfer into primary hepatocytes: Implications for genetics therapy of liver–specific functions", *"Proc. Natl. Acad. Sci."*, vol. 84, pp. 5335–5339 (1987).

Friedmann et al., "Retrovirus Vector–mediated Gene Transfer into Hepatocytes", *"Mol. Biol. Med."*, vol. 6, pp. 117–125 (1989).

Wu et al., "Targeting Genes: Delivering and Persistent Expression of a Foriegn Gene Driven by Mammalian Regulatory Elements in Vivo",*"J. Biol. Chem."*vol. 264 (No. 29) pp. 16985–16987 (1989).

Lafange–Frayssinet et al., "Alpha–Fetoprotein Gene Expression in Human Lymphoblastoid Cells and in Pha-–Stimulated Normal T–Lymphocytes", *"Biochemical and Biophysical Research Communications"*, vol. 159, No. 1, pp. 112–118 (1989).

Tsuchida, et al., "The Role of Subfractionation of Alpha–Fetoprotein in the Treatment of Pediatric Surgical Patients", *"J. of Pediatric Surgery"*, vol. 32, No. 3, pp. 514–517 (1997).

Bauvois et al., "Inhibition of γ–Glutamyl Transpeptidase Activity at the Surface of Human Myeloid Cells Is Correlated with Macrophage Maturation and Transforming Growth Factor β Production", *"Cell Growth & Differentiation"*, vol. 6, pp. 1163–1170 (1995).

Seregni et al., "Biochemical Characteristics and Clinical Applications of Alpha–Fetoprotein Isoforms", *"Anticancer Research"*, vol. 15(4) pp. 1491–1500 (1995).

Moran et al., "Hepatoid Yolk Sac Tumors of the Mediastinum: A Clinicopathologic and Immunohistochemical Study of Four Cases", *The American Journal of Surgical Pathology*, vol. 21 (No. 10), pp. 1210–1214, 1997.

Yamamasu, et al., "Role of Glutathione Metabolism and Apoptosis in the Regression if Live Hemopoiesis", *"Free Radical Biology & Medicine"*, vol. 23 (No. 1), pp. 100–109 (1997).

Leh, et al., "Cloning and expression of a novel type (III) of human γ–glutamyltransferase truncated mRNA." *FEBS Letters*, vol. 394, pp. 258–262 (1996).

Ruck et al., "Hepatic stem–like cells in hepatoblastoma: expression of cytokeratin 7, albumin and oval cell associated antigens detected by OV–1 and OV–6", *"Histopathology"*, vol. 31, pp. 324–329 (1997).

Smith et al., "Hepatic stem cells in the human liver", *"Correspondence"*, vol. 29, pp. 589–594 (1996).

Nunes et al., "Liver–Directed Gene Therapy", *"Management of Chronic Liver Disease"*, vol. 80, (5) pp. 1201–1212 (1996).

OX-43 −
OX-43 +
FIG. 2A
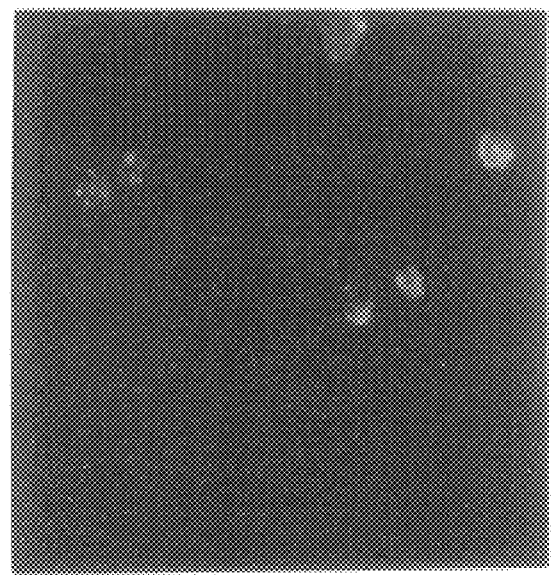
FIG. 2C
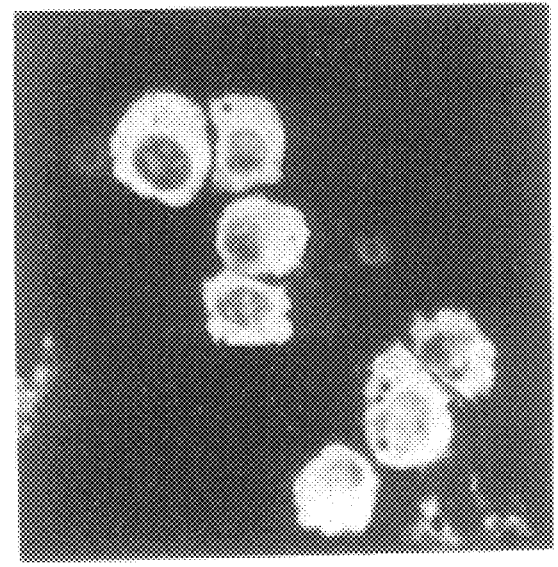
FIG. 2B

FLOW DIAGRAM OF HEPATOBLAST ENRICHMENT

LIVERS (8-9 mgs)
    ↓ DIRSPERSION WITH EGTA AND THEN COLLAGENASE

SINGLE CELL SUSPENSION PREPARATION: COLLAGENASE, EGTA, 4° C

↓ $10^7$ CELLS/8 mgs LIVER

↓ $3.2 \pm 1.3$ % ARE ALB$^+$

↓ $2.5 \pm 0.7$ % ARE AFP$^+$

↓ $87.9 \pm 2.5$ % ARE OX43/44$^+$

PANNING

RED BLOOD CELL PANNING (2X)

↓ $29 \pm 5$ % OF CELLS REMAIN

↓ $9.5 \pm 1.2$ % ARE ALB$^+$

↓ $9.8 \pm 0.9$ % ARE AFP$^+$

↓ $80.4 \pm 3.9$ % ARE OX43/OX44$^+$

OX-43/OX-44 PANNING (MYELOID AND ENDOTHELIAL CELLS)

↓ $16 \pm 4$ % OF CELLS REMAIN

↓ $14.8 \pm 3.6$ % ARE ALB$^+$

↓ $14.9 \pm 2.5$ % ARE AFP$^+$

↓ $69 \pm 10$ % ARE OX43/OX44$^+$

FLUORESCENCE ACTIVATED CELL SORTING

NEGATIVELY SORT FOR CONTAMINANT CELL POPULATIONS:

OX-43(CD)/OX-44(CD37)$^+$ CELLS = PRECURSORS AND MATURE FORMS OF HEMOPOIETIC CELLS (MYELOID, ERYTHROID) AND ENDOTHELIAL CELLS

OF REMAINING CELLS (OX-43$^-$ +OX-44$^-$ CELLS), SORT FOR CELLS VARYING IN OC.3 EXPRESSION AND GRANULARITY:

OX-43(CD)/OX-44(CD37)$^+$ CELLS = MOSTLY HEPATIC PRECURSORS, SOME RESIDUAL HEMOPOEITIC CELL CONTAMINANTS, STROMAL CELLS

OC.3$^-$, GRANULAR CELLS = COMMITTED BILE DUCT PRECURSORS (AFP$^+$, ALB$^-$)

OC.3$^-$, GRANULAR CELLS = COMMITTED HEPATOCYTE PRECURSORS (AFP$^+$, ALB$^{+++}$)

OC.3$^+$, AGRANULAR CELLS = EARLY HEPATOBLASTS (AFP$^{+++}$, ALBUMIN$^+$ AND CK 19$^-$)

FIG. 6

HEPATIC PROGENITORS AND METHOD OF ISOLATING SAME

CROSS REFERENCE TO RELATED APPLICATIONS

The present application is a Continuation of, and claims priority from application Ser. No. Ser. No. 08/757,336, filed Nov. 27, 1996 now U.S. Pat. No. 6,069,005; which was a File Wrapper Continuation of application Ser. No. 08/548,075 filed Oct. 25, 1995, abandoned; which was a File Wrapper Continuation of application Ser. No. 08/155,939 filed Nov. 19, 1993, abandoned; which was a Continuation-In-Part of application Ser. No. Ser. No. 07/741,128 filed Aug. 7, 1991, abandoned. The subject matter of these applications are incorporated herein by reference.

FIELD OF THE INVENTION

This invention relates to methods for isolating hepatoblasts and to said isolated hepatoblasts. The isolated hepatoblasts of the invention comprise liver stem cells (pluripotent precursors) and committed progenitors (precursors with only one fate) for either hepatocytes or bile duct cells. The isolated hepatoblasts of the invention may be used to treat liver dysfunction and for artificial livers, gene therapy, drug testing and vaccine production. In addition, the isolated hepatoblasts of the invention may be used for research, therapeutic and commercial purposes which require the use of populations of functional liver cells.

Unlike mature liver cells, the hepatoblasts of the invention generate daughter cells that can mature through the liver lineage and offer the entire range of liver functions, many of which are lineage-position specific. Further, the hepatoblasts of the invention have a greater capacity for proliferation and long-term viability than do mature liver cells. As a result, the hepatoblasts of the invention are better for research, therapeutic and commercial uses than mature liver cells.

BACKGROUND OF THE INVENTION

Stem cells and early progenitors have long been known to exist in rapidly proliferating adult tissues such as bone marrow, gut and epidermis, but have only recently been thought to exist in quiescent tissues such as adult liver, an organ characterized by a long cellular life span. The ability of stem cells to self-replicate and produce daughter cells with multiple fates distinguishes them from committed progenitors. In contrast, committed progenitors produce daughter cells with only one fate in terms of cell type, and these cells undergo a gradual maturation process wherein differentiated functions appear in a lineage-position-dependent process.

In adult organisms, stem cells in somatic tissues produce a lineage of daughter cells that undergo a unidirectional, terminal differentiation process. In all well-characterized lineage systems, such as hemopoiesis, gut and epidermis, stem cells have been identified by empirical assays in which the stem cells were shown to be capable of producing the full range of descendants. To date, no molecular markers are known which uniquely identify stem cells as a general class of cells, and no molecular mechanisms are known which result in the conversion of cells from self-replication and pluripotency to a commitment to differentiation and a single fate.

The structural and functional units of the hepatic parenchyma is the acinus, which is organized like a wheel around two distinct vascular beds. Six sets of portal triads, each with a portal venule, a hepatic arteriole and a bile duct, form the periphery, and the central vein forms the hub. The parenchyma, which comprises the "spokes" of the wheel, consists of plates of cells lined on both sides by the fenestrated sinusoidal endothelium. Blood flows from the portal venules and hepatic arterioles at the portal triads, through sinusoids which align plates of parenchyma, to the terminal hepatic venules, the central vein. Hepatocytes display marked morphologic, biochemical and functional heterogeneity based on their acinar location (see Gebhardt, *Pharmac. Ther.*, Vol. 53, pp. 275–354 (1990)).

Comparatively, periportal parenchymal cells are small in size, midacinar cells are intermediate in size and pericentral cells are largest in size. There are acinar-position-dependent variations in the morphology of mitochondria, endoplasmic reticulum and glycogen granules. Of critical importance is that the diploid parenchymal cells and those with greatest growth potential are located periportally. In parallel, tissue-specific gene expression is acinar-position-dependent leading to the hypothesis that the expression of genes is maturation-dependent (see Sigal et al., *Amer. J. Physiol.*, Vol. 263, pp. G139–G148 (1993)).

It is currently believed that the liver is a stem cell and lineage system which has several parallels to the gut, skin and hemopoietic systems (see Sigal et al., *Amer. J. Physiol.*, Vol. 263, pp. G139–G148 (1993); Sigal et al. *In Extracellular Matrix*, Zern and Reed, eds, Marcel Dekker, NY., pp. 507–537 (1993); and Brill et al., *Liver Biology and Pathobiology*, Arias et al., 3d eds, Raven Press, NY (1994 in press)). As such, it is expected that there are progenitor cell populations in the livers of all or most ages of animals. A lineage model of the liver would clarify why researches have been unable to grow adult, mature liver cells in culture for more than a few rounds of division, have observed only a few divisions of mature, adult liver cells when injected in vivo into liver or into ectopic sites, and have had limited success in establishing artificial livers with adult liver cells. These impasses are of considerable concern in the use of isolated liver cells for liver transplantation, artificial livers, gene therapy and other therapeutic and commercial uses.

The success of the above-listed procedures requires the use of hepatic progenitor cells (hepatoblasts) which are found in a high proportion of liver cells in early embryonic livers and in small numbers located periportally in adult livers. Because it is desirable to isolate such hepatoblasts, a need has arisen to develop a method of successfully isolating said hepatoblasts. The inventors have identified markers and developed a method for isolating hepatoblasts from the livers of animals at any age. The methods of the invention have been developed using embryonic and neonatal livers from rats, however, the method of the invention offers a systematic approach to isolating hepatoblasts from any age from any species.

The methods of the invention have been developed with embryonic livers in which there are significant numbers of pluripotent liver cells (liver stem cells) and committed progenitors (cells with a single fate to become either hepatocytes or bile duct cells). The onset of differentiation of rat parenchymal cells of the liver occurs by the tenth day of gestation. By this stage, parenchymal cells (epithelial or epitheloid cells) are morphologically homogeneous and consist of small cells with scant cytoplasm and, therefore, high nuclear to cytoplasmic ratios, with undifferentiated, pale, nuclei and a few intercellular adhesions. Most liver parenchymal cells at this stage are considered to be bipotent for bile duct cells and hepatocytes. Although they express, usually weakly, some liver-specific functions known to be activated very early in development, such as albumin and α-fetoprotein (AFP), they do not express adult-specific markers such as glycogen, urea-cycle enzymes or major urinary protein (MUP). Only a few islands of fetal cells are positive for $BDS_7$, a bile duct cell-specific marker, and none are positive for $HES_6$, a hepatocyte-specific marker (see Germain et al., *Cancer Research*, Vol. 48, pp. 4909–4918 (1988)). The hepatoblasts with scant cytoplasm and often ovoid-shaped nuclei comprise several cell populations including pluripotent liver stem cells and committed progenitors, each having only one fate for either bile duct cells or hepatocytes.

By the fifteenth day of gestation, hepatoblasts increasingly are comprised of the committed progenitors that differentiate along either the bile duct or the hepatocytic lineage. Their maturation is denoted by changes in morphology (increasing size, increasing numbers of cytoplasmic organelles and vacuoles, heterogeneous nuclear morphologies and an increase in pigmented granules), which can be distinguished readily by flow cytometric parameters. "Forward scatter" measures cell size. "Side scatter" measures cellular complexity or granularity, which is affected by the numbers of cellular organelles. Autofluorescence is dependent upon lipofuscins and other pigments that increase with maturation.

Accompanying the morphological changes are step-wise or sequential changes in expression of types of cytokeratins, various surface antigens and tissue-specific genes. Whereas the early hepatoblasts which include liver stem cells intensely express AFP and weakly express albumin, committed progenitors destined to become hepatocytes form cords of cells that lose their AFP expression, express increasingly high levels of albumin and gradually acquire hepatocyte-specific markers such as glycogen and urea cycle enzymes. Cells destined to become intrahepatic bile duct cells arise from seemingly identical hepatoblasts and retain expression of AFP, lose albumin expression and acquire cytokeratin 19 (CK 19). Initially, a string of pearl-like cells is present around the large vascular branches close to the liver hilium. Over the ensuing days, similar structures appear throughout the liver. $BDS_7$-positive cells rapidly enlarge and become more numerous with increasing developmental age. Gradually, lumina form within the structures, and by the eighteenth day of gestation, bile ductular structures are morphologically identifiable.

In order to understand liver development and the sequential changes in the expression of liver-specific genes with maturation, it is necessary to study the hepatoblasts directly. However, the study of hepatoblasts is hindered by the difficulty in isolating them since they always constitute a small portion, less than 10%, of the cell types within the liver in embryonic, neonatal, and adult life. In the embryo, the liver is the site for both hepatopoiesis (formation of liver cells) and hemopoiesis (formation of blood cells). Hempoietic cells migrate from the yolk sac into the liver during the twelfth day of gestation. Subsequently, hemopoiesis, particularly erythropoiesis, rapidly becomes one of the most prominent functions of the fetal liver with hemopoietic cells comprising 50% or more of the liver mass. In neonates, the majority of the liver cells are either hemopoietic cells or mature liver cells (hepatocytes or bile duct cells). As a result, sequential changes in parenchymal functions in intact liver are difficult to interpret because the data are confounded by the changing hemopoietic contributions. For example, it has been demonstrated that a transient decrease in parenchymal functions at day eighteen of gestation is due not to a decrease in hepatic cells or in their expression of these genes, but occurs because it is the peak of erythropoiesis, when most of the liver consists of erythroid cells. Hemopoiesis in the liver declines rapidly after birth as it transfers to the bone marrow, the site of hemopoiesis in the adult. Nevertheless, isolation of hepatoblasts in adult liver remains problematic, since they comprise a very small percentage of hepatic cells.

Because hepatoblasts can generate all developmental stages of liver cells and, therefore, offer the entire range of liver-specific functions encoded by genes activated and expressed in early to late stages of differentiation, have much greater growth potential than mature liver cells, have greater proliferative potential and offer cells with greater ability for transfection with appropriate genes (i.e., greater capacity for gene therapy), it is desirable to isolate hepatoblasts (as opposed to mature liver cells).

Currently available methods for isolation of hepatoblasts require the use of fractionation methods for cell size or cell density which are inadequate for separating the hemopoietic from the hepatopoietic precursors, require the use of cells surviving specific enzyme treatments such as pronase digestion (which have been proven to also kill hepatoblast subpopulations) or require the use of selection protocols in culture in which enrichment of the cells of interest are dependent upon differential attachment to the substratum or differential growth in specific culture media. Hence, currently available isolation methods have proven very inefficient. Moreover, identification of the parenchymal cell precursors is dependent upon assays for parenchymal-specific functions. Further, hepatoblasts dedifferentiate under most culture conditions and thereby come undetectable, or there are such a high proportion of non-relevant cells (e.g., mesenchymal cells) that the functions of interest are swamped out by those of the contaminant cell populations. In addition, dissociated liver cells readily from large aggregates via a calcium- and temperature-dependent glycoprotein-mediated process. In order to disaggregate the liver cells, it is necessary to utilize mechanical methods including vigorous pipetting and aspiration through a syringe, methods which are usually insufficient to achieve single cell suspensions and which can result in dramatically reduced viability of the cells. Hence it is desirable to develop a method of isolating fetal hepatoblasts which method maintains the hepatoblasts as a single cell suspension, does not result in cell aggregation, and is applicable to all ages.

It is therefore an object of this invention to provide methods of isolating hepatoblasts.

It is a further object of this invention to provide isolated hepatoblasts.

It is another object of this invention to provide a method of utilizing isolated hepatoblasts to treat liver dysfunction.

It is a still further object of this invention to provide methods of forming artificial livers utilizing isolated hepatoblasts.

SUMMARY OF THE INVENTION

This invention relates to isolated hepatoblasts and to methods of isolating hepatoblasts utilizing panning techniques and flow cytometry (fluorescence activated cell sorting) on cell suspensions of liver cells. Dissociated liver cells are panned and fluorescence activated cell sorted utilizing antibodies so as to greatly reduce the numbers of contaminating cell types, such as hemopoietic cells in embryonic liver or mature liver cells in adults. The cells that do not adhere to the panning dishes are negatively sorted using multiple antibodies to the contaminant cell types which leads to a cell population highly enriched for immature hepatic cell types, and then segregated into distinct subcategories of immature hepatic cell types by multiparametric fluorescence activated cell sorting. This invention is further directed to the use of isolated hepatoblasts for the treatment of liver dysfunction and for the production of artificial livers.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 6 represents a flow diagram of hepatoblast enrichment utilizing a method of the invention;

DETAILED DESCRIPTION OF THE INVENTION

Figure 1A:
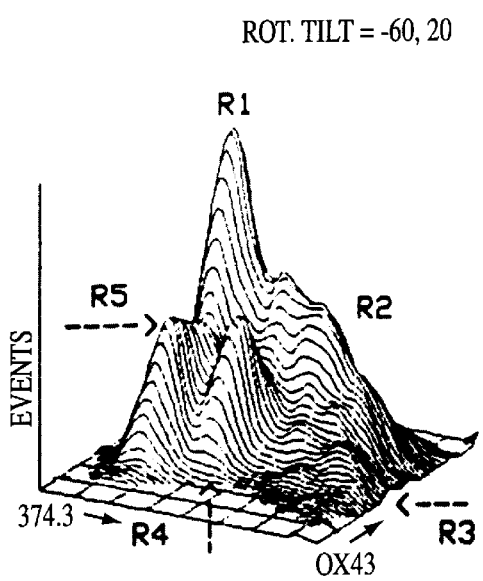
FIG. 1 represents cells from day 14 gestation livers stained for monoclonal antibodies 374.3 and OX-43, followed by FITC and PE-labeled second antibodies. Panel A is a two color density plot showing 5 populations designated R1–5 in an ungated sample. R1 and R2 are cell populations positive for OX-43, while R3–5 are negative for this marker. Panel B is a biparametric dot plot of FL2 versus SSC showing the gating parameters used to separate OX-43$^+$ from OX-43$^-$ cells. The insert shows the negative control. Panel C is a 3D plot of FL1 versus FL2 of OX-43$^-$ cells showing three distinct cell populations, R3–5, FIG. 2, panel A is a Western blot of total protein from sorted cells showing the presence of albumin containing cells exclusively in the OX-43$^-$ population. Panels B and C show indirect immunofluorescence for AFP on OX-43$^-$ (B) and OX-43$^+$ (C) cells.

This invention relates to isolated hepatoblasts and to methods of isolating hepatoblasts from dissociated liver cells utilizing panning techniques and fluorescence activated cell sorting. The isolated hepatoblasts of the invention can be used to treat liver dysfunction, to produce artificial livers, in the study of liver functions, in gene therapy, in drug testing and in vaccine production.

Livers are dissociated by enzymatic digestion, avoiding enzymes such as pronase that adversely affect hepatoblasts, and then kept in solutions which are chilled and which contain chelating agents such as EGTA, which results in cells that can be sustained as single cells. Dissociated liver cells are then panned with antibodies to greatly reduce the numbers of contaminating cell types (hemopoietic cells, including red blood cells, endothelial cells and other mesenchymal cells in embryonic and neonatal liver, and mature liver cells, hepatocytes, bile duct cells, endothelial cells and other mesenchymal cells in adult liver). Panning alone, although rapid, is inefficient and does not yield very pure cell populations. However, it is used to rapidly reduce the number of non-hepatoblast cells. The cells that do not adhere to the panning dishes are then segregated by fluorescence activated cell sorting, a technology with very high accuracy and efficiency. The combination of the rapid panning methodology with the accuracy of the fluorescence activated cell sorting results in highly purified cell populations with good viability.

In embryonic and neonatal livers, the contaminant cell types reduced through panning protocols are erythroid, myeloid and other hemopoietic cell types and endothelia (mesenchymal cell types). The panning steps lead to a cell population enriched for immature hepatic cell types. In adult livers, the contaminant cell types are mature hepatocytes, bile duct cells, endothelia and some hemopoietic cell populations.

Panned cells are also sorted for multiple markers that distinguish distinct subcategories of hepatic precursor cell populations. The markers identified are (a) the extent of granularity as measured by side scatter on fluorescence activated cell sorting, wherein more immature cell populations are more agranular, and increasing granularity correlates with increasing maturity; (b) the extent of autofluorescence, wherein increasing autofluorescence correlates with increasing maturity; and/or (c) the expression of a hepatic cell marker (such as the oval cell marker OC.3, which is detected by monoclonal antibody 374.3).

Liver cells which do not express hemopoietic or endothelial cell antigens recognized by monoclonal antibodies OX-43 and/or OX-44 (which recognize myeloid cells and endothelia) and which do not express antigens recognized by a monoclonal antibody to an erythroid antigen comprise the hepatoblasts of the invention. The hepatoblasts of the invention include three categories of immature liver cells:

(1) More granular cells, which are $OC.3^+$, are committed bile duct precursors. These cells are also $AFP^+$, $albumin^+$ and $CK\ 19^+$.

(2) More granular cells, which are $OC.3^-$, are committed hepatocyte precursors. These cells are also $AFP^+$, $albumin^{+++}$, and $CK\ 19^-$.

(3) Agranular cells, which are $OC.3^+$, are very immature hepatic precursors. These cells are also $AFP^{+++}$, $albumin^+$ and $CK\ 19^-$.

This invention is further directed to the use of hepatoblasts isolated by the methods of the invention. The isolated hepatoblasts of the invention can be used for to treat liver dysfunction. For example, hepatoblasts can be injected into the body, such as into the liver or into an ectopic site. Whole liver transplantation, which requires costly and dangerous major surgery, can be replaced by a minor surgical procedure which introduces hepatoblasts in vivo either into the liver via the portal vein or at an ectopic site such as the spleen. In addition, hepatoblasts can be used in bioreactors or in culture apparatus to form artificial livers. Further, hepatoblasts can be used in gene therapy, drug testing, vaccine production and any research, commercial or therapeutic purpose which requires liver cells of varying extents of maturity.

EXAMPLE I

Fischer 344 rats with known durations of pregnancy were obtained from Harlan Sprague Dawley, Inc. (Indianapolis, Ind.) and maintained in the animal facility of the Albert Einstein College of Medicine, Bronx, N.Y. on a standard rat chow diet with 12 hour light cycles. By convention, the first day of gestation is defined as day 0. Use of animals was in accordance with the NIH Policy on the care and use of laboratory animals and was approved by the Animal Care and Use Committee of the Albert Einstein College of Medicine.

In order to isolate fetal liver cells, pregnant rats at the fourteenth day of gestation were euthanized with ether and the embryos were removed intact and placed into ice cold $CA^{+2}$-free Hank's Balanced Salt Solution containing 0.04% DNAse, 0.8 mM $MgCl_2$, 20 mM HEPES, pH 7.3 (HBSS). Livers were then dissected from the fetuses and placed into fresh ice-cold HBSS. After all tissues were collected and non-hepatic tissue removed, HBSS-5 mM EGTA was added to a final EGTA concentration of 1 mM. The livers were moved to a 50 ml conical centrifuge tube by pipette, gently triturated 6 to 8 times to partially disaggregate the tissue and then centrifuged at 400 g for 5 minutes at 4° C. All subsequent centrifugation steps were performed at the same settings. The supernatant was removed and the pellet of cells and tissue was resuspended in 50 ml 0.6% Collagenase D (Boehringer Mannheim, Indianapolis, Ind.) in HBSS containing 1 mM $CaCl_2$, gently triturated and then stirred at 37° C. for 15 minutes in an Erlenmeyer flask. The dispersed cells were pooled, suspended in HBSS containing 1 mM EGTA and filtered through a 46 µm tissue collector (Bellco Glass, Inc., Vineland, N.Y.). The cell suspension was centrifuged and the cells were resuspended in HBSS supplemented with MEM amino acids, MEM vitamins, MEM non-essential amino acids, insulin (10 µg/ml), iron-saturated transferrin (10 µg/ml), free fatty acids (7.6 mEq/L, as described by Chessebeuf et al., 1984, Nu-Chek-Prep, Elysian, Minn.), trace elements, albumin (0.1%, fraction V, fatty acid free, Miles Inc., Kankakee, Ill.), myo-inositol (0.5 mM) and gentamicin (10 µg/ml, Gibco BRL, Grand Island, N.Y.) (HBSS-MEM). Cell number and viability were determined by hemacytometer and trypan blue exclusion.

In order to remove erythroid cells, panning dishes were prepared according to the procedure of Wysocki and Sato (1978) using a rabbit anti-rat RBC IgG (Rockland Inc., Gilbertsville, Pa.). Antibodies (0.5 mg/dish) diluted in 9 ml of 0.05 M Tris pH 9.5 were poured on 100 $mm^2$ bacteriological polystyrene petri dishes (Falcon, Lincoln Park, N.J.). The dishes were swirled to evenly coat the surface and incubated at room temperature for 40 minutes. The coated dishes were washed four times with PBS and once with HBSS containing 0.1% BSA prior to use.

Three milliliters of the cell suspension containing up to $3 \times 10^7$ cells were incubated at 4° C. for 10 minutes in the dishes coated with the rabbit anti-rat RBC IgG. The non-adherent cells were removed by aspiration and the plates were washed three times with HBSS-0.1%BSA-0.2 mM EGTA and centrifuged. The cell pellet was resuspended in HBSS-MEM and RBC panning was repeated. Following the second RBC panning cell number and viability were determined again.

The cells recovered after RBC panning were then labeled in suspension by incubating with mouse monoclonal antibody OX-43 (1/200=15 µg/ml, MCA 276, Bioproducts for Science, Indianapolis, Ind.) and monoclonal antibody 374.3 (1/500–1/750, a gift of R. Faris and D. Hixon, Brown University, Providence, R.I.) simultaneously at 4° C. for 40 minutes. OX-43 recognizes an antigen on endothelial cells, a subpopulation of macrophages and erythroid cells (see Barclay, *Immunology*, Vol. 42, pp. 593–600 (1981) and Robinson et al., *Immunology*, Vol. 57, pp. 231–237 (1986)) and 374.3 recognizes oval cells, bile duct cells and hemopoietic cells (see Hixon et al., *Pathology: Liver Carcinogenesis*, pp. 65–77 (1990)). Second antibodies were PE-conjugated anti-mouse IgG, heavy chain specific (Southern Biotechnology Inc., Ala.) and FITC-conjugated anti-mouse IgM, heavy chain specific (Sigma Chemical Co., St. Louis, Mo.). Negative controls included cells without label and cells labeled with mouse isotype controls.

Cells before and after sorting were maintained at 4° C. and in HBSS-MEM. After completion of the antibody labeling, propidium iodide at final concentration of 10 µg/ml was added to each of the sample tubes. Fluorescence Activated Cell Sorting was performed with a Becton Dickinson FACSTAR$^{plus}$ (San Jose, Calif.) using a 4 W argon laser with 60 mW of power and a 100 µm nozzle. Fluorescent emission at 488 nm excitation was collected after passing through a 530/30 nm band pass filter for FITC and 585/42 nm for PE. Fluorescence measurements were performed using logarithmic amplification on biparametric plots of FL1 (FITC) vs FL2 (PE). Cells were considered positive when fluorescence was greater than 95% of the negative control cells.

For measurement of physical characteristics of the cells, FACSTAR$^{plus}$ parameters were FSC gain 8 and SSC gain 8. These settings allowed all cells to be visualized on scale. HBSS was utilized as sheath fluid. For analysis, a minimum of 10,000 events were measured. List mode data were acquired and analyzed using LysisII software. Dead cells were gated out using propidium iodide fluorescence histograms on unlabeled cells.

For determination of positivity to a single antibody dot plots of fluorescence versus side scatter were used. Density plots FL1 versus FL2 were used to select populations with respect to expression of both antigens. A sort enhancement module was utilized for non-rectangular gating and use of multiparametric gating to select populations of interest.

Shorted cells from day fourteen of gestation from all populations were plated in a serum-free, hormonally-defined medium with αMEM as the basal medium to which the following components were added: insulin (10 μg/ml); EGF (0.01 μg/ml, Upstate Biotechnology, Lake Placid, N.Y.); growth hormone (10 μU/ml); prolactin (20 mU/ml); Tri-iodothyronine ($10^{-7}$ M); dexamethasone ($10^{-7}$ M); iron saturated transferrin (10 μg/ml); folinic acid ($10^{-8}$ M, Gibco BRL, Grand Island, N.Y.), free fatty acid mixture (7.6 mEq/L, as described by Chessebeuf et al., 1984, Nu-Chek-Prep, Elysian, Minn.); putrescine (0.02 μg/mi); hypoxanthine (0.24 μg/ml); thymidine (0.07 μg/ml); bovine albumin (0.1%, fraction V, fatty acid free, Miles Inc. Kankakee, Ill.); trace elements; $CuSO_4.5H_2O$ (0.0000025 mg/l), $FeSO_4.7H_2O$ (0.8 mg/l), $MnSO_4.7H_2O$ (0.0000024 mg/l), $(NH_4)_6Mo_7O_{24}.H_2O$ (0.0012 mg/l), $NiCl_2.6H_2O$ (0.000012 mg/l), $NH_4VO_3$ (0.000058 mg/l), $H_2SeO_3$ (0.00039 mg/l); Hepes (31 mM) and Gentamicin (10 μg/ml, Gibco BRL, Grand Island, N.Y.). Reagents were supplied by Sigma Chemical Company, St. Louis, Mo., unless otherwise specified. The trace element mix was a gift from Dr. I. Lemishka, Princeton University, N.J.

Culture dishes as well as cytospins of various cell suspensions were fixed with ice-cold ethanol or acetone. After blocking with PBS containing 1% BSA for 30 minutes at room temperature, the fixed cells were studied by indirect immunofluorescence using the following primary antibodies: polyclonal rabbit-anti-rat albumin (United States Biochemical Corporation, Cleveland, Ohio), rabbit-anti-mouse AFP antiserum (ICN Biomedical, In., Costa Mesa, Calif.), monoclonal mouse-anti-human cytokeratin 19 (Amersham Life Science, Arlington Heights, Ill.), polyclonal rabbit-anti-human IGF II receptor (a gift of Dr. Michael Czech, University of Worchester, Mass.), mouse monoclonal anti-rat-Thy-1 (OX-7, Bioproducts for Science, Indianapolis, Ind.), monoclonal mouse-anti-desmin (Boehringer Mannheim, Indianapolis, Ind.), and 258.26, a monoclonal mouse-anti-rat antibody identifying postnatal hepatocytes as well as some fetal liver parenchymal cells (a gift of Drs. R. Faris and D. Hixon, Brown University, R.I.). Second antibodies included species specific Rhodamine conjugated antibodies corresponding to the primary antibodies. Negative controls consisted of cells stained with mouse or rabbit IgG or mouse isotype controls. Freshly isolated adult hepatocytes were used as positive controls for albumin staining. Gamma-glutamyltranspeptidase (GGT) was assayed by immunochemistry on ethanol fixed cells using the method described by Rutenberg et al., *J. Hist. Cyt.*, Vol. 17, pp. 517–526 (1969).

In order to perform Northern blot analysis for the presence of specific mRNA, total RNA was extracted from sorted cells using the guanidinium isothiocyanate method, as described by Chomcznyski et al., *Anal. Biochem.*, Vol. 162, pp. 156–159 (1987)). RNA samples were resolved by electrophoresis through 1% agarose formaldehyde gels in 3-(N-morpholino)-propanesulfonic acid buffer (see Maniatis et al., *Molecular Cloning: A Laboratory Manual*, pp. 191–193 (1982)). The RNA was then transferred to Gene Screen (New England Nuclear, Boston, Mass.), and the filters were prehybridized and hybridized with the appropriate probes. The cDNA clones complementary to specific mRNAs were radioactively labeled by primer extension with 32P dCTP as described by Feinberg et al., *Anal. Biochem.*, Vol. 137, pp. 266–267 (1984). The cDNAs used in hybridization were rat albumin (a gift of Dr. Zern, Jefferson University, Philadelphia, Pa.), and mouse α-fetoprotein, (Dr. Tighlman, Princeton, N.J.), GGT (obtained from Dr. M. Manson, MRC Medical Research Council, Surrey, UK) and PG19. Autoradiograms were scanned with a Quantimat densitometer (Model 920; Manufacturer's Cambridge Instrument). The data for each of the genes was normalized to that for the common gene 18S (J. Darnell, Rockefeller University, New York, N.Y.).

In order to perform Western blot analysis, total protein samples from various sorted cells were loaded on a 10% polyacrylamide minigel. Loading was normalized for equal cell numbers, 100,000 cells per slot. Electrophoresis followed by electroblotting to nitrocellulose membranes (Schleicher and Schuell, Keene, N.H.) was performed. The blots were blocked overnight in 2% dry milk solution at 4° C. and assayed for albumin using a rabbit-anti-rat albumin antiserum diluted 1:800 in the blocking solution for 1 hour at room temperature, followed by a one hour incubation with horseradish-peroxidase conjugated anti-rabbit IgG (Amersham Life Science, Arlington Heights, Ill.) diluted 1:50 in blocking solution. Detection was achieved by incubation of blots with ECL-chemiluminescence kit reagents (Amersham Life Science, ARlington Heights, Ill.) for 1 minute and subsequent autoradiography.

Forty-eight well plates were coated with type I collagen extracted from rat tail tendon as described by Reid, *Methods in Molecular Biology*, The Humana Press, Inc., Vol. 5, pp. 237–276 (1990). Sorted cells at densities between 50,000 to 100,000 cells/cm$^2$ were plated per well. Following an overnight attachment period, the medium with the non-adhering cells was gently removed and replaced by fresh medium. A complete medium change was performed every 24 hours. The cells were cultured at 37° C. in a fully humidified atmosphere containing 5% $CO_2$ and were observed daily. After four days in culture, cells were fixed with ice-cold ethanol and stained in situ by Immunofluorescence for albumin, AFP, CK 19 and IGF II receptor and by immunochemistry for GGT, as described below.

Livers from fourteenth day gestation embryos isolated by the EGTA-collagenase digestion yielded single cell suspensions and a negligible number of cell aggregates. Cellular viability was greater than 95% as determined by exclusion of trypan blue. Cell yield was 2.62±0.31×10$^6$ cells per liver. The original cell suspension was subjected to two steps of immunoadherence ("panning") using rabbit anti-rat RBC IgG coated polystyrene dishes. Cellular recovery after completion of two panning steps was 51% (±8%), but varied somewhat with different lots of antibodies.

Figure 1B:
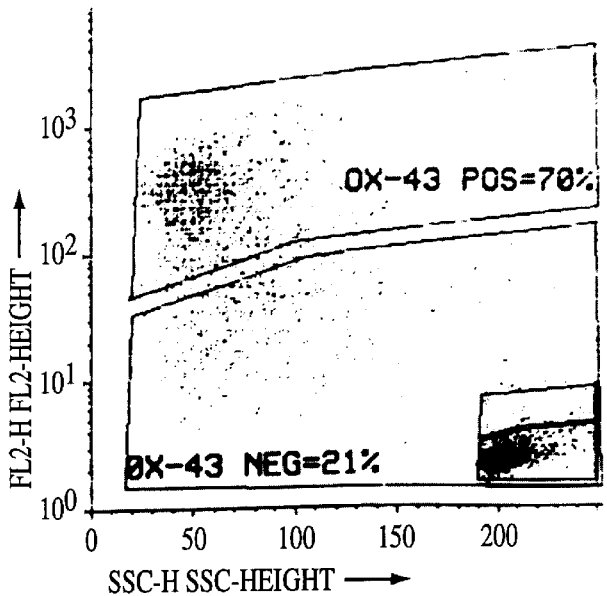
Figure 1C:
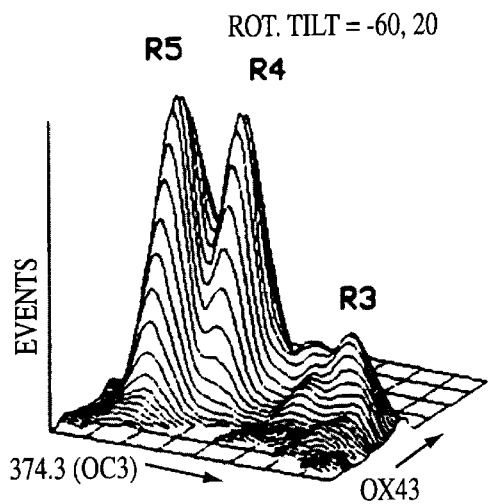

The cells recovered after RBC-panning were stained in suspension with a mixture of two antibodies: an antibody raised against "oval cells" (monoclonal antibody 374.3) and a commercially available antibody known to recognize endothelial, as well as some erythroid and myeloid cells in the rat (monoclonal antibody OX-43). Following incubation with the proper FITC and PE labeled second antibodies, cells were analyzed for their fluorescence patterns. As shown in FIG. 1, panel A, when fluorescence intensities for both antigens were plotted against each other, five distinct populations, referred to as R1 through R5, were observed. With minor variations in the percentage of each population, the distribution of cells to form the five populations was extremely reproducible. The small differences could be explained by variations in the percent recovery of cells after RBC panning.

Initial analyses of sorted cells by immunofluorescence revealed the presence of albumin and AFP positive cells in one of the OX-43 positive cell populations (R2). These larger and more complex cells comprised approximately 5–10% of cells in this gate. However, when freshly sorted R2 cells were viewed under the epi-fluorescent microscope, these larger cells appeared to be negative for OX-43 (no PE labeling). The parenchymal cells in the liver have a significant degree of autofluorescence, which increases with maturation of the liver, in parallel to the increase in cellular complexity, as measured by the side scatter parameter on the FACS. It was therefore postulated that it is due to this phenomenon that some parenchymal cells appear in the region of the OX-43-positive cells, although not expressing the antigen. To pursue this hypothesis, positivity to OX-43 was determined accurately on side scatter (cellular granularity) versus PE fluorescence, as measured on the FL2 scale (FIG. 1, panel B), and OX-43-positive and negative cells were sorted and characterized. To determine the accuracy of the sorts, post-sort acquisitions of the sorted cells were performed using the same instrument settings. Typical post-sort purity (i.e., percentage of cells from a shorted population that appeared in the same region when analyzed again after the sort) was >90%.

Sorted cells from both OX-43 positive and negative gates were assayed for expression of liver specific genes by Western blot analysis and by indirect immunofluorescence. As shown in FIG. 2, panel A, there was a minimal amount of albumin in the OX-43-positive cell fraction, detected by Western blotting, as compared with the OX-43-negative cells. No AFP positive cells could be shown by indirect immunofluorescence on cytospins of sorted OX-43-positive cells, as opposed to 30% of OX-43-negative cells expressing the fetal liver marker (see FIG. 2, panels B and C). It was concluded that at day 14 of gestation, all fetal liver parenchymal cells are OX-43-negative. Therefore, in order to achieve "cleaner" gates, OX-43-positive and negative cells were separated on a SSC versus FL2 plot and studied separately.

When OX-43 positive cells were electronically gated out and the remaining cells viewed on a FL1 versus FL2 plot, three distinct populations were readily detected (see FIG. 1, panel C), corresponding to R3–5 in the ungated cell suspension. All of the cells in R3 were 374.3-positive whereas 30% of the cells in R4 were positive for that marker. R5 cells did not express OC.3. Expression of various liver-specific and other genes was studied on sorted cells from R3–5. The results are summarized in Table 1, below.

TABLE 1

Characterization of sorted cells by immunofluorescence and by histochemistry

| | R1 | R2 | R3 | R4 | R5 |
|---|---|---|---|---|---|
| Albumin | neg | neg | 1% pos | 75–80% pos | neg |
| AFP | neg | neg | 2% pos | 70% pos | neg |
| GGT | neg | neg | 1% pos | 75% | neg |
| IGF-IIr | 20% | 1% | 2% | 85% | neg |
| CK 19 | neg | neg | 2–3% | neg | neg |
| Desmin | <1% + | 1–2% +++ | neg | neg | <1% + |
| 258.26 | neg | neg | neg | neg | neg |
| Thy-1 | 2% | 10% | 75% | 10% | 5% |

Figure 3:
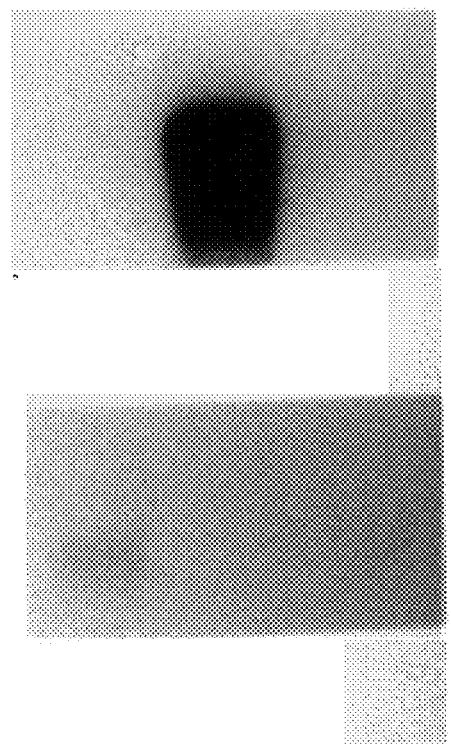
FIG. 3 represents cells from R3–5 which were sorted after gating out all OX-43$^+$ cells and total RNA prepared by the guanidinium isothiocyanate method. The Northern blot demonstrates expression of albumin in R4, while serglycin is expressed by R3 cells.
Figure 4:
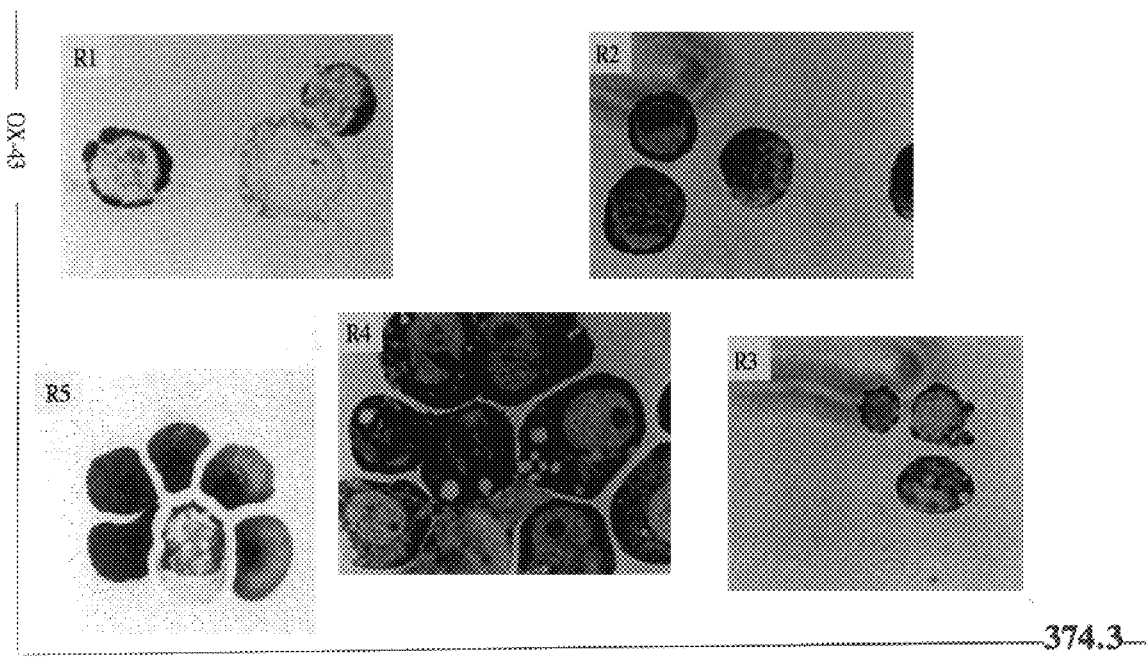
FIG. 4 represents cells which were gated to separate populations positive and negative to OX-43 and then further separated to 5 populations based on their fluorescence on biparametric density plots of FL1 versus FL2. Freshly sorted and cytospun cells were stained for morphology by Diff-Quik staining kit. Original magnification—100X.

About 2–3% of R3 cells (less than 0.2% of the total ungated cell suspension) were intensely stained for albumin and AFP. They also expressed GGT and CK 19, markers of the bile duct lineage. However the majority of the cells appeared to be small, blast-like cells, and did not express liver specific genes but expressed classical hemopoietic markers such as Thy-1 and serglycin (see Table 1 and FIGS. 3 and 4). Most of the liver parenchymal cells were found in the R4 gate (see Table 1 and FIG. 3). The vast majority of the cells expressed albumin, AFP and GGT, all markers of fetal liver parenchyma. No hemopoietic or fat storing cell markers were detected in that gate. The cell population designated R5 is a heterogeneous one (see FIG. 4), comprising mainly two cell types: (1) cells that morphologically appear to be normoblasts; and (2) simple small cells that did not express parenchymal liver genes. The ratio between these two cell types varied somewhat and was dependent on the efficiency of the RBC panning.

When all of the OX-43 negative cells were gated out, two distinct populations were observed on an FL1/FL2 plot. As expected, no parenchymal liver markers were detected in these cells. A few of R2 cells intensely stained with the antibody against desmin, an intermediate filament usually expressed in fat storing cells. Morphologically, most of R2 cells appeared to be early erythroid precursors (see FIG. 4), while 10% of them expressed Thy-1. In the R1 gate were two morphologically distinct cell types (see FIG. 4). The majority were small, blast-like and did not express any of the markers tested. The others, about 20% of the cells in this gate, were larger cells with a pale cytoplasm and expressed the receptor for IGF-II. Very few cells from R1 stained for Thy-1.

Figure 5A:
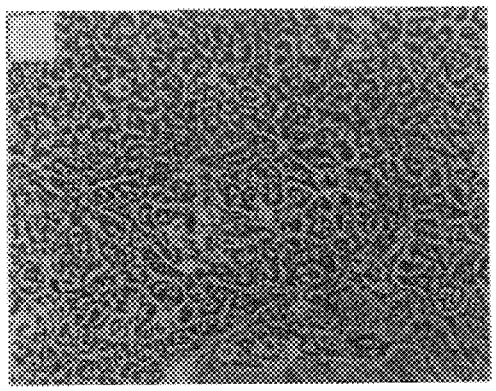
FIG. 5 represents a population highly enriched for fetal liver parenchymal cells which was obtained by FACS (R4 cells after exclusion of all OX-43$^-$) and 5×10$^4$ cells/cm$^2$ plated on type I collagen coated dishes in a serum free, hormonally defined medium. Panel A is a phase micrograph showing a typical epithelial colony and very few mesenchymal cells after 4 days in culture (original magnification—50X). Panel B is an indirect in situ immunofluorescence showing incorporation of BrdU in the nuclei of about 25% of the cultured parenchymal cells after 24 hours in culture (original magnification—50X. Panel C is a phase micrograph of panel B.
Figure 5B:
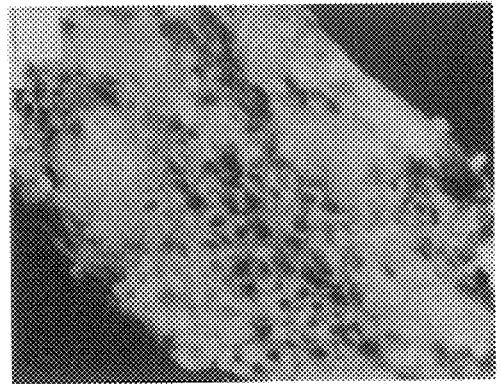
Figure 5C:
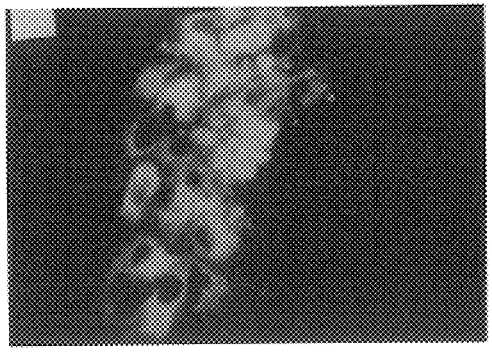
Figure 5D:
Figure 5E:
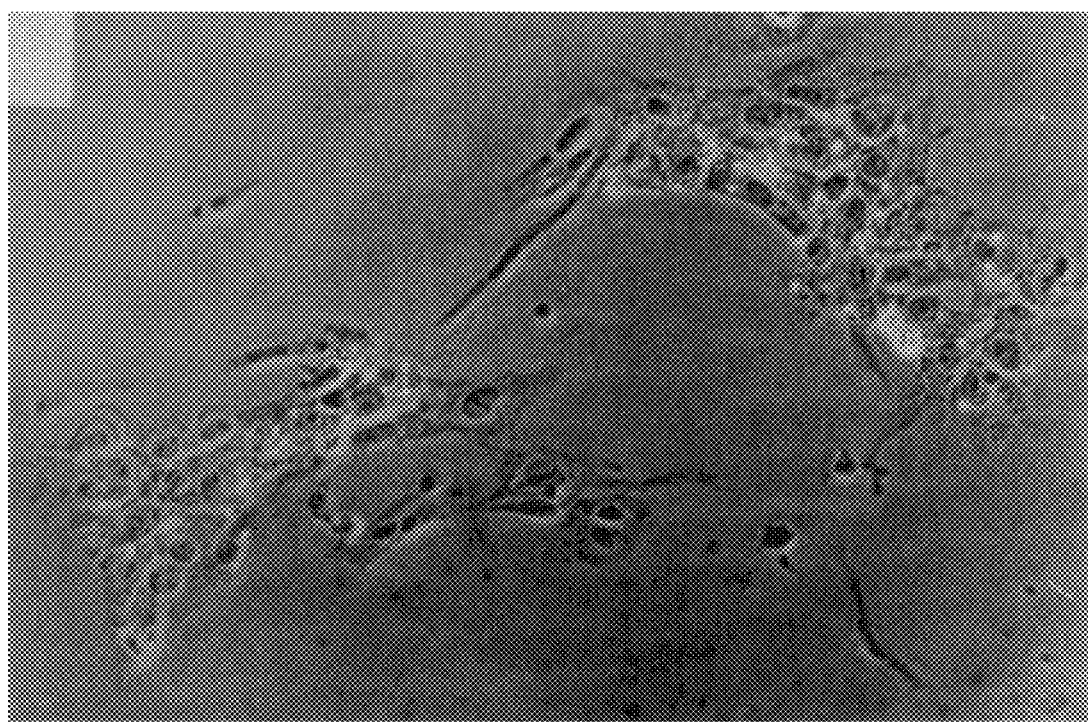
Figure 5F:
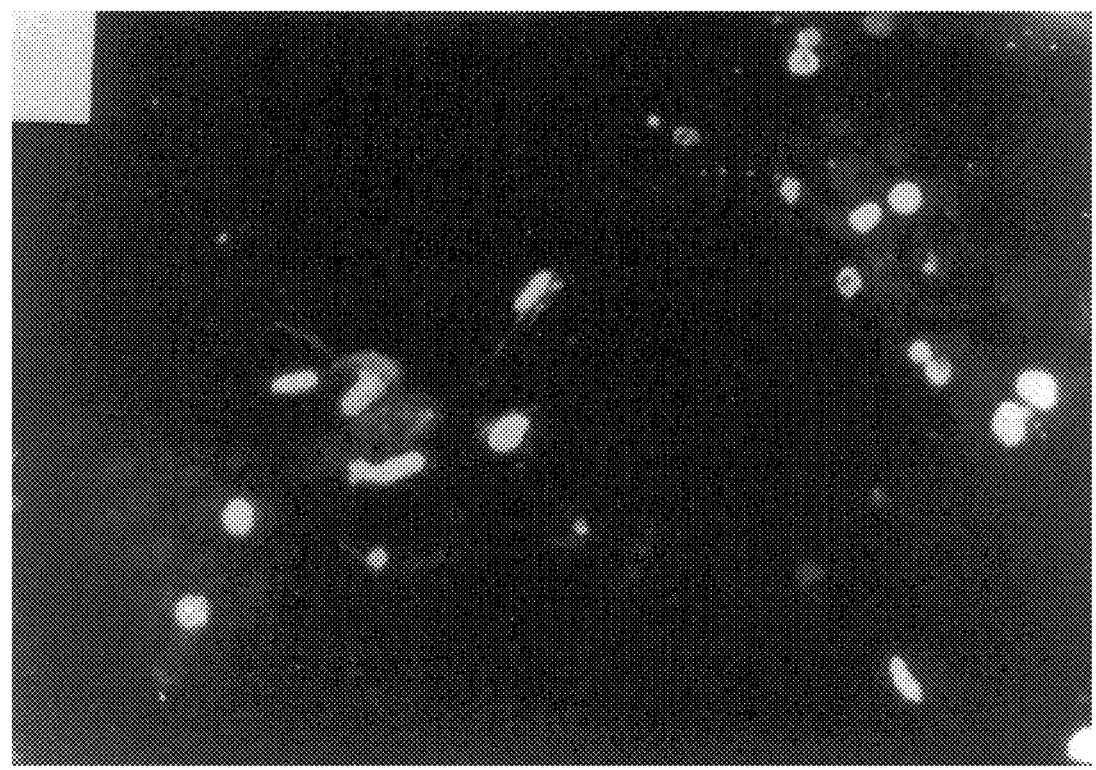

Sorted cells from all 5 populations were cultured for 4 days to determine in vitro fates. When plated at high density under the conditions described, R4 cells yielded clusters of epithelial cells surrounded by very few scattered stromal cells (see FIG. 5A and Table 2 below).

TABLE 2

Characterization of R4 cells after 4 days in culture

| Marker | Epithelial Cells | Stromal Cells |
|---|---|---|
| Albumin | + | neg |
| AFP | ± | neg |
| GGT | ++ | neg |
| CK 19 | +(30%) | neg |
| 258.26 | neg | neg |
| IGF IIr | + (perinuclear staining) | + (perinuclear staining) |

Cell division was clearly evident both in the epithelial as well as the stromal components of the culture. On the second day of the culture 25±5% of the epithelial cells showed incorporation of bromo-deoxy-uridine (BrdU) following a one hour incubation with a medium containing BrdU (see FIG. 5A and B). When RBC-panned but not sorted day 14 gestation cells were plated under similar conditions, they survived for at least 10 days (data now shown). However, cultures of sorted R4 cells deteriorated quickly. The epithelial cells lost their classical polygonal shape and elongated, similarly to what is seen in primary cultures of adult hepatocyte in the presence of serum. Moreover, when stained in situ for albumin, AFP and GGT, cultured R4 cells exhibited a gradual decline in these liver-specific genes, whereas RBC-panned day 14 gestation cells maintained their gene expression under similar conditions (data not shown). IGF-II receptor remained clearly detected in the golgi of the cultured epithelial as well as the stromal cells. About 30% of the cultured R4 cells showed staining for CK 19, a cytokeratin present in bile duct cells and not in adult hepatocytes.

When cells from all other four populations were plated under the same conditions, only few scattered fibroblast-like cells (but not epithelial colonies) were observed. Despite the liver-parenchymal characteristics of some R3 cells, epithelial colonies from these cells could not be obtained under similar plating conditions. This may have been due to low density of the epithelial cells in this gate. These cells aggregated in suspension, survived for about 48 hours and then died. Coating the dishes with type I or type IV collagen, fibronectin or laminin alone or in combination did not improve attachment or survival of these cells (data now shown).

EXAMPLE II

Fisher 344 rats with known durations of pregnancy were obtained from Harlan Sprague Dawley, Inc. (Indianapolis, Ind.) and maintained in the animal facility of the Albert Einstein College of Medicine, Bronx, N.Y. on a standard rat chow diet with 12 hour light cycles. By convention, the first day of gestation is defined as day 0. Use of animals was in accordance with the NIH Policy on the care and use of laboratory animals and was approved by the Animal Care and use Committee of the Albert Einstein College of Medicine.

Pregnant rats at the fifteenth day of gestation were euthanized with ether, and the embryos were delivered. Livers were then dissected from the fetuses, weighed, placed into ice-cold, $Ca^{+2}$-free Hank's Balanced Saline Solution containing 0.8 mM $MgCl_2$, 20 mM HEPES, pH 7.3 (HBSS), and gently agitated at room temperature for 1 minute. After removal of non-hepatic tissue, livers were gently triturated and then stirred at 37° C. for 10 to 15 minutes in an Erlenmeyer flask with 0.6% type IV collagenase (Sigma Chemical Co., Lot 11H6830, St. Louis, Mo.) in HBSS containing 1 mM $CaCl_2$ and 0.06% DNAse I (Boehringer Mannheim, Indianapolis, Ind.). At 5 minute intervals, tissue fragments were allowed to sediment at 1 g. The supernatant was recovered and fresh collagenase solution added. The dispersed cells were pooled, suspended in HBSS containing 5 mM EGTA and filtered through a 46 μm tissue collector (Bellco Glass, Inc., Vineland, N.Y.) under 1 g. The resultant cell suspension was centrifuged at 4° C. for 5 minutes under 450 g. The cell pellet was resuspended in HBSS containing 0.2 mM EGTA and 0.5% BSA (HBSS-EGTA-0.5% BSA), and the cell number was estimated with a Coulter Counter (Coulter Electronics, Inc., Hialeah, Fla.). Cell viability was assessed by exclusion of 0.04% trypan blue, and an aliquot of the suspension was centrifuged in a tared microfuge tube at 450 g for 5 minutes.

In order to immunoadhere hemopoietic and endothelial cells onto antibody-coated polystyrene dishes, panning dishes were prepared according to the procedure of Wysocki and Sato. The antibodies employed included rabbit anti-rat RBC IgG (Inter-cell Technologies, Inc., Hopewell, N.J.) and goat IgG directed towards mouse whole IgG molecule (M-3014, Sigma, St. Louis, Mo.). Antibodies (0.5 mg/dish) diluted in 10 ml of 0.05 M Tris pH 9.5 were poured on 100 $mm^2$ bacteriological polystyrene petri dishes (Falcon, Lincoln Park, N.J.) to evenly coat the surface and incubated at room temperature for 40 minutes. The coated dishes were washed four times with PBS and once with HBSS containing 0.1% BSA prior to use.

Three milliliters of the cell suspension containing up to $3 \times 10^7$ cells were incubated at 4° C. for 10 minutes in the dishes coated with the rabbit anti-rat RBC IgG. The supernatant containing non-adherent cells was removed by gentle aspiration while tilting and swirling, combined with three washes of 7 ml HBSS-EGTA-0.1% BSA, and centrifuged at 4° C. for 5 minutes under 450 g. Cells from two dishes were pooled and repanned with a fresh dish coated with rabbit anti-rat RBC IgG. The non-adherent cells were then removed as above and resuspended with HBSS-EGTA-0.5% BSA to a concentration of $1 \times 10^7$/ml. The enriched hepatoblasts were then incubated simultaneously at 4° C. for 40 minutes with mouse monoclonal antibody OX-43 (15 μg/ml, MCA276, Serotec, Indianapolis, Ind.) and monoclonal antibody OX-44 (18 μg/ml, MCA371, Serotec, Indianapolis, Ind.). OX-43 recognizes an antigen on macrophages, endothelial cells and red blood cells, and OX-44 recognizes the membrane-glycoprotein CD53 that is present on all rat myeloid cells as well as peripheral lymphoid cells, and is related to the human leukocyte antigen CD37. After washing to remove excess antibody, cells were panned at 4° C. for 10 minutes in a dish coated with the goat anti-mouse whole IgG antibody, and non-adherent cells were removed as described above.

Next, cytospins of the various cell suspensions were fixed with either ice-cold ethanol or alcohol, acetone and carbo-wax 1540 (Fix-Rite, Richard-Allan Medical Industries, Richland, Mich.), After blocking, the fixed cells were immunostained by indirect immunofluorescence or the biotin/streptavidin method using β-galactosidase (BioGenex, San Ramon, Calif.) with rabbit anti-rat albumin IgG (USB Corp., Cleveland, Ohio) or rabbit anti-mouse AFP antiserum (ICN ImmunoBiologicals, Lisle, Ill.) as primary antibodies. Negative controls consisted of cells stained with the primary antibodies omitted. Positive controls for albumin staining were done with freshly isolated adult hepatocytes.

In order to perform Northern blot analysis, total RNA was extracted from the cells before and after panning and from the cells adherent to the panning dishes using the guanidinium isothiocyanate method. RNA samples were resolved by electrophoresis through 1% agarose formaldehyde gels in 3-(N-morpholino)-propanesulfonic acid buffer, then transferred to Gene Screen (New England Nuclear, Boston, Mass.), which was prehybridized, and then hybridized with the appropriate probes. The cDNA clones complementary to specific mRNAs were radioactively labeled by primer extension with $^{32}P$ dCTP. The cDNAs used were rat albumin, mouse AFP and mouse 18S (J. Darnell, Rockefeller University, NY). Autoradiograms were scanned with a Quantimat densitometer (Model 920; Manufacturer's Cambridge Instrument). The data for each of the genes was normalized to that for the common gene 18S.

To perform FACS analysis and sorting for hemopoietic and endothelial cell markers at day 15 gestation, cell suspensions at various stages of enrichment were analyzed by flow cytometry in the FACS facility of the Albert Einstein College of Medicine, Bronx, N.Y. Cells were resuspended to $1 \times 10^7$ cell/ml and incubated at 4° C. for 40 minutes with OX-43 with and without OX-44, followed by FITC-conjugated anti-mouse IgG (heavy chain specific, Southern Biotech, Birmingham, Ala.) at 4° C. for 40 minutes. Cells stained only with FITC-conjugated anti-mouse IgG served as negative controls.

Flow cytometric analysis was performed on a Becton-Dickinson FACScan (San Jose, Calif.) with a 15 mW air-cooled argon laser. Cell sorting was performed with a Becton Dickinson FACSTAR$^{plus}$ (San Jose, Calif.) using a 4 W argon laser with 60 mW of power and 100 µm nozzle. In both instances fluorescent emission at 488 nm excitation was collected after passing through a 530/30 nm band pass filter for FITC. Fluorescence measurements were performed using logarithmic amplification. Cells were considered positive when fluorescence was greater than 95% of the negative control cells. For measurement of physical characteristics of the cells, the detector value was E-1 for forward scatter (FSC) with mid-range amplification. For side scatter (SSC) the detector value was mid-range with an amplification of 1. Equivalent FACSTAR$^{plus}$ parameters were FSC gain 4 and SSC gain 8. These settings allowed all cells to be visualized on scale. FSC and SSC gating were performed using linear amplification, dividing both parameters into 256 arbitrary units (A.U.). For analysis, at least 10,000 events were measured. List mode data were acquired and analyzed using LysisII software. Cells before and after sorting were maintained at 4° C. and in HBSS supplemented with insulin, transferrin, free fatty acids, trace elements, albumin, and gentamicin as detailed for supplements added to the HDM.

Next, multiparametric flow cytometric analysis of hemopoietic and endothelial markers was performed with respect to the oval cell antigen OC.3. Isolated cells were labeled with a combination of OX-43 and OX-44 (mouse IgGs) and monoclonal antibody 374.3 (mouse IgM, Hixson and Faris, Brown University, Providence, R.I.) followed by FITC-conjugated goat anti-mouse IGG (heavy chain specific, So Biotech, Birmingham, Ala.) and PE-conjugated goat anti-mouse IgM (heavy chain specific, So Biotech, Birmingham, Ala.). Cells stained only with FITC-conjugated anti-mouse IgG and PE-conjugated anti-mouse IgM served as negative controls. Cells were evaluated both for extent of fluorescence for one of the probes and by side scatter, a measure of cellular complexity (extent of cytoplasmic organelles).

Cells from day 15 gestation livers were panned against rat red blood cell antibody, and the epithelial-enriched cell suspension was plated in a serum-free hormonally defined medium with αMEM as the basal medium to which the following components were added: insulin (10 µg/ml); EGF (0.01 µg/ml, Upstate Biotechnology, Lake Placid, N.Y.); growth hormone (10 µU/ml); prolactin (20 mU/ml); glucagon (10 µg/ml); Triiodothyronine ($10^{-7}$M); dexamethasone ($10^{-7}$M); iron saturated transferrin (10 µg/ml); folinic acid ($10^{-8}$M, Gibco BRL, Grand Island, N.Y.), free fatty acid mixture (0.76 mEq/l, a modification of the method described by Chessebeuf, Nu Check-Prep, Elysian Minn.); putrescine (0.02 µg/ml); hypoxanthine (0.24 µg/ml); thymidine (0.07 µg/ml); bovine albumin (0.1%, fraction V, fatty acid free, Miles Inc., Kankakee, Ill.); trace elements: $CuSO_4.5H_2O$ (0.0000025 mg/l), $FeSO_4.7H_2O$ (0.8 mg/l), $MnSO_4.7H_2O$ (0.0000024 mg/), $(NH_4)_6Mo_7O_{24}.H_2O$ (0.0012 mg/l), $NiCl_2.6H_2O$ (0.000012 mg/l), $NH_4VO_3$ (0.000058 mg/l), $H_2SeO_3$ (0.00039 mg/l); Hepes (31 mM) and Gentamicin (10 µg/ml, Gibco BRL, Grand Island, N.Y.). Reagents were supplied by Sigma Chemical Company (St. Louis, Mo.) unless otherwise specified. The trace element mix was a gift from Dr. I. Lemishka, Princeton University, N.J.

Twenty-four well plates were coated with type IV collagen extracted from EHS tumors. Panned cells at densities between 12,500 and 25,000 cells per $cm^2$ were plated per well and allowed to attach for four to five hours after which the medium with the non-adhering cells were gently removed and replaced by fresh medium. Cells were cultured at 37° C. in a fully humidified atmosphere containing 5% $CO_2$ and were observed daily for 5 to 16 days. A complete medium change was performed every 48 hours.

At various time points after initiation of the culture, cells were fixed with ice-cold ethanol and stained in situ by immunochemistry or by immunofluorescence for albumin and AFP.

The weight of the liver at the 15th day of gestation was 9.1±1.3 mg. Collagenase treatment digested the liver completely, and only minimal particulate matter was excluded by the tissue sieve. The number of cells obtained at this step was $1.07 \times 10^7$/liver, and the weight of the dissociated cells was 8.6±1.1 mg/liver, 95% of the whole organ weight. The suspension consisted almost entirely of isolated single cells with occasional small aggregates that increased in size and number in the absence of EGTA and at temperatures greater than 4° C. Viability by trypan blue exclusion was greater than 90%.

After each panning, phase contrast microscopy demonstrated that the adherent cells exhibited an erythroid morphology. Only rare cells were positive for albumin by immunochemistry. After panning with the rabbit anti-rat red blood cell antibody-coated dishes to remove red blood cells and then with the goat anti-mouse whole molecular IgG antibody-coated dishes to reduce the numbers of OX43/OX44$^+$ cells, the non-adherent cells constituted 29±5% and 16±4%, respectively, of the cell number of the freshly dispersed fetal liver (original suspension). Panning proved successful for liver tissue at all fetal and early neonatal ages, although the variation in hemopoietic constituents with developmental age resulted in differing degrees of enrichment (data not shown). Also, the efficiency of the RBC panning procedure varied with the antibody lot. With antibodies of poor efficiency for direct panning, however, indirect immunoadherence was successful for the cells labeled in suspension followed by panning with anti-rabbit IgG coated petri dishes.

Figure 7A:
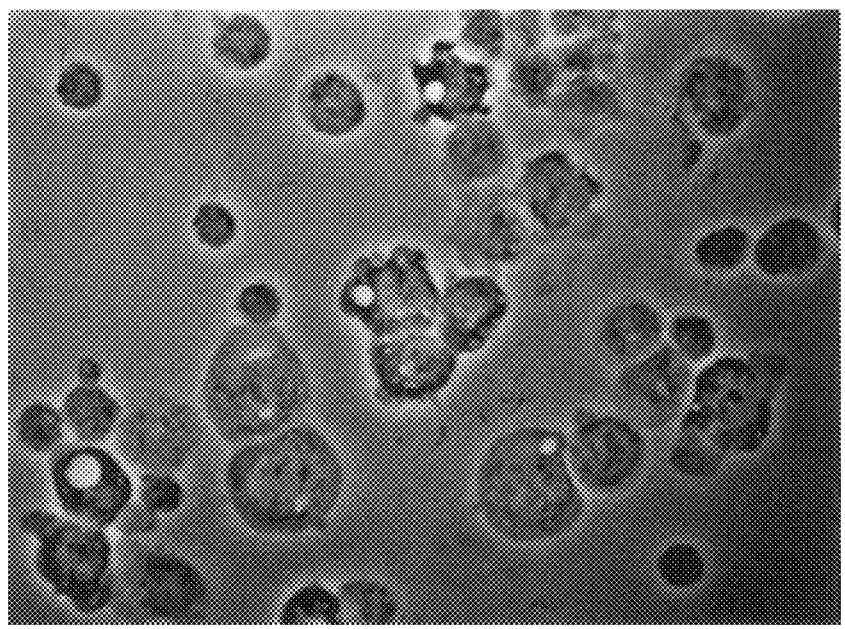
FIG. 7 panel A represents phase contrast microscopy and panel B represents immunofluorescence for AFP of hepatoblasts at gestation day 15, AFP positive cells ranged in morphology from small cells with oval nuclei and scant cytoplasm that were only slightly larger than the hemopoietic cells to cells with larger amounts of vacuolated cytoplasm. Negative controls consisted of cells stained with rabbit IgG as a primary antibody.
Figure 7B:
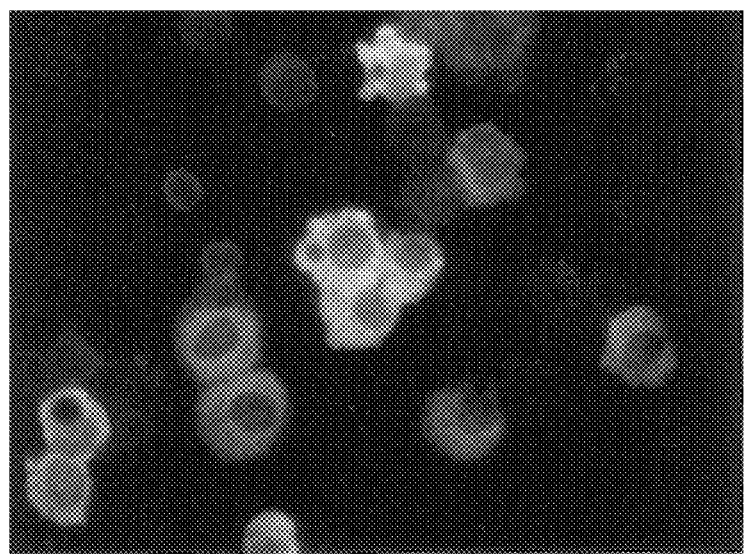

On phase contrast microscopy following liver dispersion the predominant cell type was a small, red cell consistent in morphology with that of an early erythroid cell. Also present were larger, vacuolated cells. Immunocytochemistry demonstrated that the vast majority of the vacuolated cells as well as occasional smaller, oval-shaped cells were strongly positive for albumin and AFP (see FIG. 7). The proportions of albumin and AFP positive cells at various stages of enrichment are shown in (see Table 3 below and FIG. 6).

TABLE 3

Characteristics of the E15 liver cellular suspension at various stages of enrichment

| Markers | Percent of cells positive in the Original Suspension | Percent of cells positive after RBC Panning | Percent of cells positive after IgG Panning |
|---|---|---|---|
| Albumin[1] | 3.2 ± 1.3 | 9.5 ± 1.2 | 14.8 ± 3.6 |
| Alpha-fetoprotein | 2.5 ± 0.7 | 9.8 ± 0.9 | 14.9 ± 2.5 |
| MoAb OX-43[2] | 76.6 ± 5.8 | 70.5 ± 6.1 | ND |
| MoAb OX-43/44[2] | 87.9 ± 2.5 | 80.4 ± 3.9 | 69.0 ± 10.0 |
| % cells remaining of original suspension | 100 | 29 ± 5 | 16 ± 4 |

ND = Not done
[1]Immunocytochemistry with the biotin/streptavidin method using β-galactosidase (BioGenex, San Ramon, CA) with primary antibody omitted as negative control.
[2]Cells were considered positive when fluorescence was greater than 95% of the negative control cells by FACS analysis.

Figure 8:
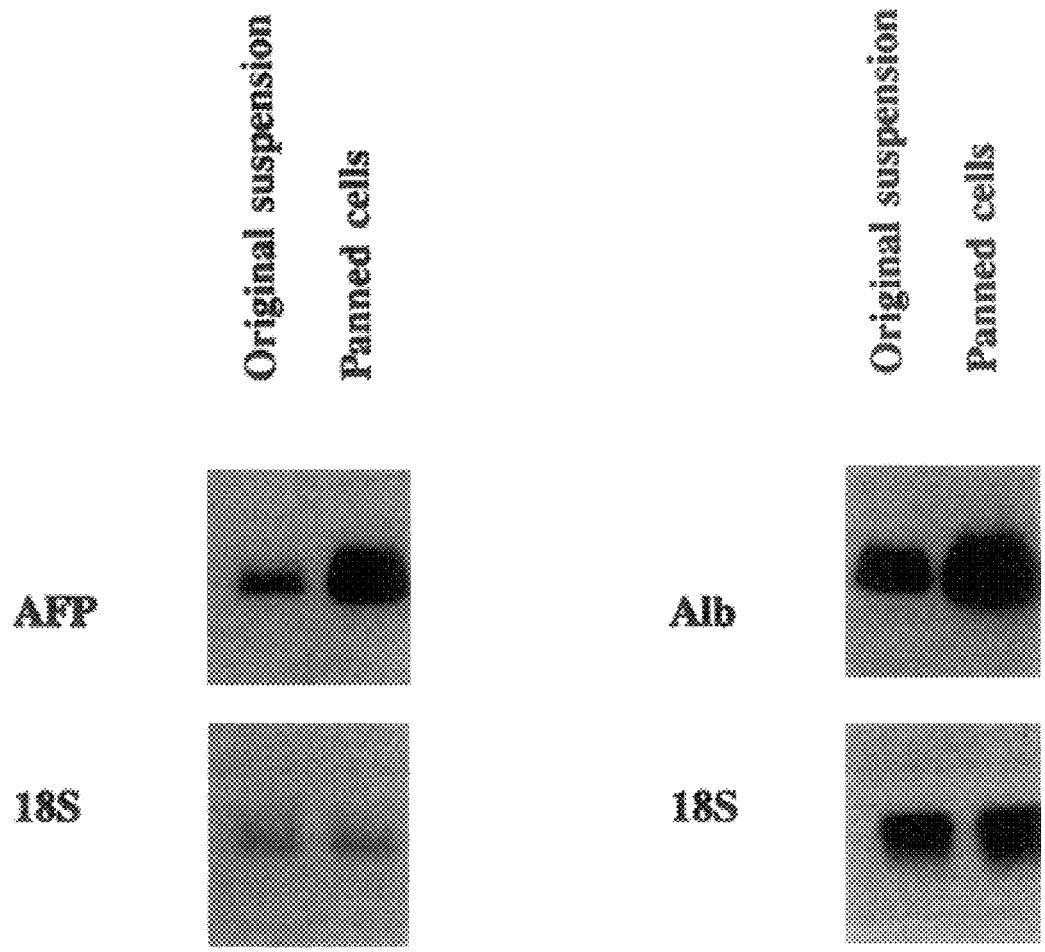
FIG. 8 represents Northern blot analysis of total RNA (5 $\mu$g/lane) from freshly isolated fetal liver cells before and after panning and hybridized with cDNAs encoding α-fetoprotein and albumin. Lane 1 shows freshly isolated fetal liver cells. Lane 2 shows cell preparation after panning 2X with anti-rat RBC antibody. Also shown are blots for 18S, used as an internal control for total RNA loading.

Northern blot analysis for liver-specific genes (albumin and AFP) was done on cells before and after panning and is shown in FIG. 8. The cells after panning were enriched up to 5-fold for AFP mRNA and 2-fold for albumin mRNA, a finding indicative both of the success of the panning procedures and of the high concentrations of hepatoblasts (as opposed to mature hepatocytes). Negligible levels of albumin and no AFP mRNA were evident in the cells adherent to the panning dishes.

To determine the efficiency with which hemopoietic and endothelial cells were removed, cells at various stages of enrichment were analyzed by flow cytometry for the presence of OX-43 which recognizes macrophages, endothelial cells and red blood cells and for the presence of OX-44 which recognizes myeloid and peripheral lymphoid cells. The results are shown in FIG. 6 and in Table 3. The percentage of cells positive for OX-43/OX-44 in the original cell suspension was 87.9±2.5%. The combination of panning procedures with anti-rat RBC IgG and anti-mouse whole IgG antibodies removed 84% of the cells. Although 69±10.0% of the non-adherent cells were still positive for the OX-43/44 markers, the percentage of hepatoblasts was enriched dramatically (5-fold). Although additional panning could have reduced the OX-43/44+ cell population even further, it was found that the cell numbers had been reduced sufficiently by panning to enable the FAC sorting to complete the process of eliminating the OX-43/44+ cells.

When examined by flow cytometry, fetal liver cells constituted a heterogeneous population with respect to FSC, a measure of cell size, and SSC, a measure of cytoplasmic complexity. Cytologically, there was a broad range in cell size (5 to 15 μ by Coulter Counter, data not shown), but cell size was not found to be useful in separating hemopoietic from parenchymal precursors. Rather, the populations were best segregated using SSC. The definition of granular versus agranular cells was made based on a linear scale for side scatter using biparametric plots of fluorescence versus side scatter. Based on the population profiles, 50 A.U. usually demarcated the agranular from the granular cells.

Figure 9A:
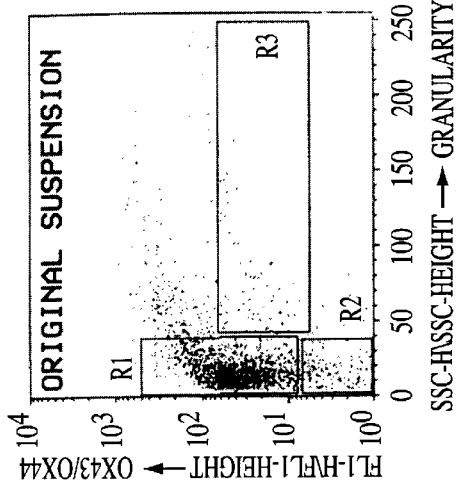
FIG. 9 represents biparametric analysis of fetal rat liver cells presented as side scatter (SSC), a measure of cytoplasmic complexity, versus log fluorescence for OX-43 and OX-44. Panel A shows unstained cells; panel B shows the cells immediately following isolation (original suspension); and panel C shows the cells after final panning. The vast majority of the cells immediately after isolation were agranular and positive for the markers (R1 cell population). With enrichment, the population of granular cells (SSC>50 A.U.) which were negative for the OX43/OX44 markers (R3 cell population) increased. Sorting for this population revealed that 75% were positive for AFP. The demarcation between positive and negative is higher for the granular than the agranular populations due to greater autofluorescence of the granular cells.
Figure 9B:
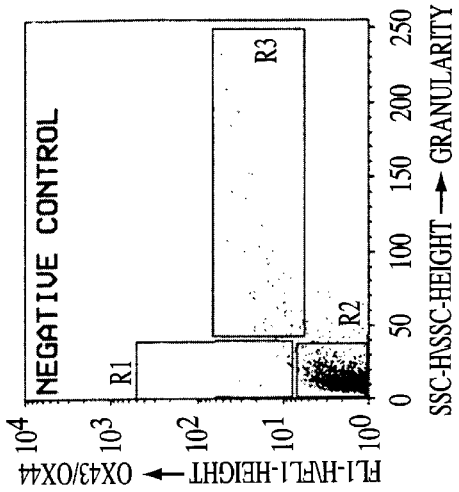
Figure 9C:
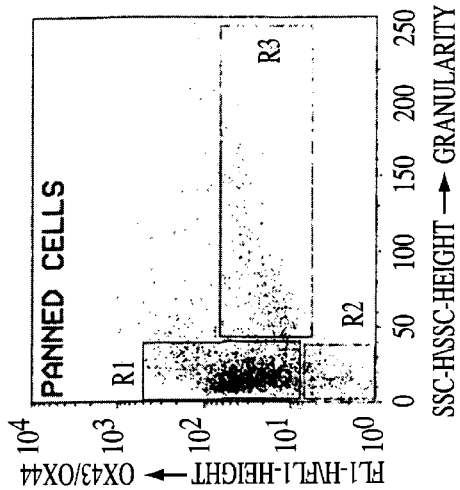

Using SSC versus fluorescence, the fetal liver cells could be isolated into three populations: agranular cells (the R1 population), which were positive for the endothelial and/or myeloid markers (OX43/X44), and agranular (R2) and granular (R3) cells negative for the OX43/OX44 markers (see FIG. 9). The demarcation between positive and negative was higher for the granular than the agranular populations due to greater autofluorescence of the granular cells. Analysis of the sorted FACS populations demonstrated that less than 1% and 3.0±0.7% of the cells in the R1 and R2 populations, respectively, were positive for AFP. However, 75.1±4.7% of the granular cells negative for the markers (R3) were positive for AFP by immunocytochemistry (see Table 4 below).

TABLE 4

Characteristics of cell fractions on FACS

|  | R1 | R2 | R3 |
|---|---|---|---|
| Fluorescence for 276 and/or 371[1] | positive | negative | negative |
| Granularity (A.U.)[2] | agranular | agranular | granular |
| % AFP positive[3] | <1% | 3.0 ± 0.7% | 75.1 ± 4.7% |

[1]Cells were considered positive when fluorescence was greater than 95% of the negative control cells by FACS analysis.
[2]50 A.U. demarcated the agranular from the granular cells using FACS parameters of FSC gain 4 and SSC gain 8.
[3]Immunocytochemistry with the biotin/streptavidin method using β-galactosidase (BioGenex, San Ramon, CA) with primary antibody omitted as negative control.

Double image analysis of the R1 cell population, the only one analyzed having OX-43/X44+ cells, indicated extensive overlap of OX-43/44 positive and OC.3 positive cells. The FACS pattern for OX-43/OX-44 was similar for all gestational ages except for a subtle increase in the R1 (and concomitant decrease in the R3 population) with increasing gestational age due to increasing hepatic erythropoiesis (data not shown). Analysis of the sorted cell population that was positive for OX-43/44, regardless of expression of OC.3 or of granularity, revealed that morphologically most were hemopoietic precursor cells and were negative for AFP. Of the granular, OX-43/44⁻ cells (the R3 cell population), most of which were AFP+, approximately 30% were OC.3+. A small population of cells (R2 in Table 4) that were OX43/44⁻, agranular, and AFP+ have not been evaluated for OC.3 expression.

Figure 10:
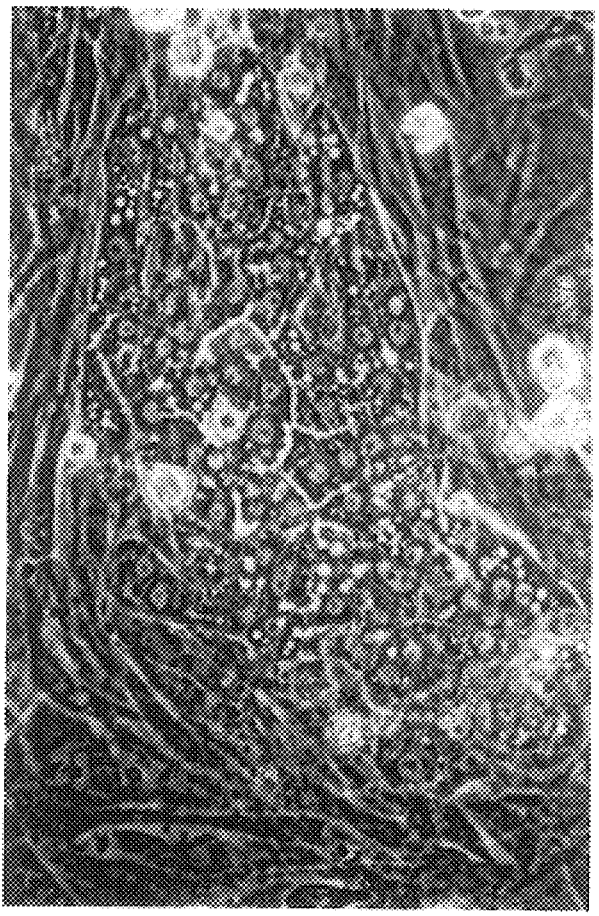
FIG. 10 represents day 15 gestation cells enriched for hepatoblasts by panning out RBCs cultured for 5 days on type IV collagen in serum-free hormonally defined medium. The cells exhibited typical epithelial morphology including formation of bile canaliculi. Surrounding epithelial cells are fibroblast-like cells. Bar=25$\mu$.
Figure 11:
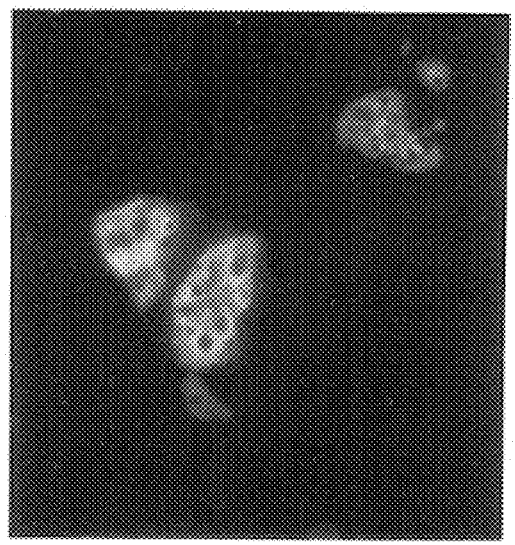
FIG. 11 represents small epithelial islands showing positive staining for albumin by in situ immunofluorescence after 16 days in culture. The fibroblast-like cells surrounding them are negative for the presence of albumin. Bar=100$\mu$.

Cell preparations from day 15 gestation enriched by panning for hepatoblasts were plated on type IV collagen-coated dishes and in the serum-free, hormonally defined medium as described. Within a day after plating, the epithelial cells reaggregated and attached to the matrix as small cell clusters. Plating efficiencies of up to 60% were obtained (data not shown). The cells were organized into islands of typical parenchymal cells forming close cell-cell contacts and bile canaliculi, surrounded by non-epithelial, fibroblast-like cells (see FIG. 10). After 4–5 days in culture the parenchymal cell components were gradually overgrown by the non-parenchymal cells. However, residual clusters of hepatoblasts remained positive for albumin and AFP for up to 16 days in culture, as assessed by in situ immunochemistry or immunofluorescence (see FIG. 11). In a few experiments in which glucagon was omitted from the culture medium, no noticeable morphological difference was observed, and the cells expressed albumin and AFP when stained in situ by immunofluorescence or immunochemistry (data not shown). This observation is attributed to relative glucagon resistance of the fetal hepatoblasts.

The inventors have developed methods, incorporating panning technologies and multiparametric FAC sorting, which isolate cell populations highly enriched for liver parenchymal cell precursors. The methods of this invention have been found by the inventors to be applicable to the isolation of hepatic precursor cells from liver from gestational age day 13 through the early neonatal period. The liver dispersion procedure described yields a population of predominantly single cells with greater than 90% viability, and at gestation day 15, 95% of the whole organ weight is recovered. The panning procedures remove up to 84% of the total cell number, and simultaneously enrich the hepatoblast population by 5-fold. The increase in the parenchymal-specific gene expression of albumin and AFP was illustrated by Northern blot analysis of the cells before and after panning, and the procedure's specificity demonstrated by analysis of the cells adherent to the panning dishes. Similarly, the enrichment was confirmed by the in vitro data in which there was a dramatic increase in the number of cell colonies expressing albumin and AFP after panning compared to the original suspension. Furthermore, the plating efficiency after panning was significantly higher (up to 60%) compared to previously reported values of 6 to 10%. Though the hepatoblasts still remain a minor population after panning procedures, it is important to consider that the standard in situ hepatocyte perfusion protocols yields a population containing, on average, 37.7% hepatocytes.

The advantage of this protocol in comparison with previous methods which involved attachment of dispersed liver cells to culture dishes, low-speed differential centrifugation, and culture in arginine-deficient medium are several-fold. Isolate hepatocytes rapidly lose tissue-specific gene regulation in vitro. As a result, in procedures requiring cell attachment to matrix, measurement of parenchymal-specific function, such as protein or mRNA content, might not reflect in vivo levels. Dissociated fetal hepatoblasts also readily form large aggregates via a calcium and temperature-dependent, glycoprotein-mediated process. As early as gestation day 14, high levels of a cell membrane protein which is thought to be uvomorulin (E-cadherin) were present on hepatoblasts. This tendency for aggregation explains the ability of low speed differential centrifugation to enrich for relatively large (E19) hepatoblasts, especially in the presence of $Ca^{2+}$ and at temperatures greater than 4° C. To disaggregate the hepatoblasts, mechanical methods including vigorous pipetting and aspiration through a syringe have been employed but found to be insufficient, leading to difficulties with further analyses which require a single cell suspension such as FACS.

The tendency of the cells to aggregate is prevented by maintaining the cells at 4° C. and by removing calcium with EGTA, interfering with CAM-mediated aggregation. The advantage of maintaining the cells as a single cell suspension is two-fold. First, measurement of parenchymal specific functions can be determined on a cellular basis, overcoming the physiologically irrelevant changes in hemopoietic cell population. Second, procedures such as FACS which demand a single cell suspension can be easily performed.

Though gestation day 15 hepatoblasts appear larger than the non-parenchymal cells, side scatter rather than forward scatter on the FACS proved to be a better discriminator in separating the various populations, presumably because even gestation day 12 hepatoblasts, which contain vacuoles, mitochondria and abundant endoplasmic reticulum, are relatively complex. In addition, side scatter proved a reasonable measure of cellular maturity. In general, hepatoblasts of greater granularity were more mature morphologically and biochemically (data not shown).

Hence, FACS analysis was employed to examine the expression of the oval cell marker, OC.3, which has been proposed to identify liver stem cells. With multiparametric FACS analysis for OC.3 or OX-43/44 expression in combination with gating for cells of particular levels of granularity, the inventors were able to subdivide the populations into non-parenchymal cells (hemopoietic, endothelial, and stromal cells) versus parenchymal cell precursors that were AFP$^+$. Moreover, the inventors were able to evaluate the expression of the OC.3 antigen in the various subpopulations. At gestation day 15, most agranular, OX43/44$^+$ cells proved to be hemopoietic cells, largely erythroid cell populations. Of the granular, OX43/44 cell population, which were predominantly AFP$^+$, approximately 30% of the cells were OC.3$^+$ and probably represented bile duct cell precursors, whereas the OC.3 cells were probable hepatocyte precursors. However, a small percentage of agranular, OX43/44$^-$ cells were AFP$^+$.

In comparison to the hemopoietic field, the liver stem cell field is still in its infancy. However, the ability to isolate specific populations by FACS sorting using these parameters with subsequent in vitro and in vivo fate studies will greatly aid in identifying the liver stem cell. Furthermore, this technology is applicable to the study of all aspects of liver stem cell biology including the biliary epithelium, carcinogenesis, regeneration, aging and tissue-specific gene expression.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of isolating hepatic progenitors from liver comprising:
   (a) preparing a single cell suspension of liver cells;
   (b) panning said suspension utilizing antibodies specific for hemopoietic cells, mesenchymal cells, mature liver cells, or combinations thereof, to remove said hemopoietic cells, mesenchymal cells, and mature liver cells from said suspension;
   (c) performing fluorescence activated cell sorting utilizing said antibodies so as to remove hemopoietic cells, mesenchymal cells, and mature liver cells, from said cell suspension; and
   (d) performing multiparametric fluorescence activated cell sorting on said suspension utilizing at least one antibody to a hepatic cell marker, side scatter forward scatter, autofluorescence, or combinations thereof, such that the cells remaining in said suspension are enriched hepatic progenitors.

2. The method of claim 1 wherein the antibody specific for hemopoietic cells is a monoclonal antibody.

3. The method of claim 2 wherein said monoclonal antibody is OX-43 and/or OX-44.

4. The method of claim 1 wherein said hepatic cell marker is OC.3.

5. The method of claim 1 wherein said single cell suspension contains an agent capable of removing calcium from liver cell surface.

6. The method of claim 1 wherein said single cell suspension contains EGTA.

7. The method of claim 1 wherein said single cell suspension contains an enzyme capable of dissociating liver cells.

8. The method of claim 1 wherein said single cell suspension contains collagenase.

9. The method of claim 1 wherein said single cell suspension is chilled.

10. The method of claim 1 wherein said single cell suspension is at a temperature of between about 2 and 20° C.

11. The method of claim 1 wherein the liver is neonatal liver.

12. The method of claim 1 wherein the liver is embryonic liver.

13. The method of claim 1 wherein the liver is adult liver.

14. A method of isolating hepatic progenitors from liver comprising:

(a) preparing a single cell suspension of liver cells; and (b) panning said suspension utilizing antibodies specific for hemopoietic cells, mesenchymal cells, mature liver cells, or combinations thereof, to remove said hemopoietic cells, mesenchymal cells, and mature liver cells, or combinations thereof, from said suspension such that the cells remaining in said suspension are enriched hepatic progenitors.

15. The method of claim 14 which further comprises performing fluorescence activated cell sorting utilizing said antibodies.

16. The method of claim 14 which further comprises performing multiparametric fluorescence activated cell sorting on said suspension utilizing at least one antibody to a hepatic cell marker, side scatter, forward scatter, autofluorescence or combinations thereof.

17. The method of claim 14 wherein the antibody specific for hemopoietic cells is a monoclonal antibody.

18. The method of claim 17 wherein said monoclonal antibody is at least one of OX-43 and OX-44.

19. The method of claim 14 wherein said hepatic cell marker is OC.3.

20. The method of claim 14 wherein said single cell suspension comprises an agent capable of removing calcium from liver cell surface.

21. The method of claim 14 wherein said single cell suspension comprises EGTA.

22. The method of claim 14 wherein said single cell suspension comprises an enzyme capable of dissociating liver cells.

23. The method of claim 14 wherein said single cell suspension contains collagenase.

24. The method of claim 14 wherein said single cell suspension is chilled.

25. The method of claim 14 wherein said single cell suspension is at a temperature of between about 2 and 20° C.

26. The method of claim 14 wherein the liver is neonatal liver.

27. The method of claim 14 wherein the liver is embryonic liver.

28. The method of claim 14 wherein the liver is adult liver.

29. The method of claim 1 wherein the mesenchymal cells comprise endothelial cells.

30. The method of claim 1 wherein the mature liver cells comprise at least one of hepatocytes and bile duct cells.

31. The method of claim 14 wherein the mesenchymal cells comprise endothelial cells.

32. The method of claim 14 wherein the mature liver cells comprise at least one of hepatocytes and bile duct cells.

* * * * *